United States Patent
Dichtel et al.

(10) Patent No.: US 9,556,085 B2
(45) Date of Patent: Jan. 31, 2017

(54) GRAPHENE NANORIBBONS DERIVED FROM POLY(PHENYLENE ETHYNYLENE) POLYMER, METHODS OF MAKING SAME, AND USES THEREOF

(75) Inventors: William R. Dichtel, Ithaca, NY (US); Hasan Arslan, Ithaca, NY (US); Fernando J. Uribe-Romo, Orlando, FL (US)

(73) Assignee: Cornell University, Ithaca, NY (US)

(*) Notice: Subject to any disclaimer, the term of this patent is extended or adjusted under 35 U.S.C. 154(b) by 243 days.

(21) Appl. No.: 14/113,457

(22) PCT Filed: Apr. 27, 2012

(86) PCT No.: PCT/US2012/035368
§ 371 (c)(1),
(2), (4) Date: Apr. 4, 2014

(87) PCT Pub. No.: WO2012/149257
PCT Pub. Date: Nov. 1, 2012

(65) Prior Publication Data
US 2014/0212668 A1    Jul. 31, 2014

Related U.S. Application Data

(60) Provisional application No. 61/479,998, filed on Apr. 28, 2011.

(51) Int. Cl.
B32B 5/16 (2006.01)
C07C 2/84 (2006.01)
(Continued)

(52) U.S. Cl.
CPC ............... *C07C 2/84* (2013.01); *B82Y 10/00* (2013.01); *B82Y 30/00* (2013.01); *B82Y 40/00* (2013.01); *C01B 31/0446* (2013.01); *C07C 15/20* (2013.01); *C08G 61/02* (2013.01); *C08G 61/10* (2013.01); *H01B 1/04* (2013.01); *H01L 31/1884* (2013.01); *H01L 51/0045* (2013.01);
(Continued)

(58) Field of Classification Search
CPC .................... C01B 31/0438; C01B 31/0446
USPC ................... 428/402; 977/734, 788, 932
See application file for complete search history.

(56) References Cited

U.S. PATENT DOCUMENTS 7,887,888 B1    2/2011    Sidorov et al.
2010/0028681 A1    2/2010    Dai et al.
(Continued)

FOREIGN PATENT DOCUMENTS

WO    2010137592    2/2010

OTHER PUBLICATIONS

Cai et al., Atomically precise bottom-up fabrication of graphene nanoribbons, Nature, vol. 455, Jul. 2010, pp. 470-473.*
(Continued)

*Primary Examiner* — Holly Le
(74) *Attorney, Agent, or Firm* — Hodgson Russ LLP

(57) ABSTRACT

Provided are graphene nanoribbons (GNRs), methods of making GNRs, and uses of the GNRs. The methods can provide control over GNR parameters such as, for example, length, width, and edge composition (e.g., edge functional groups). The methods are based on a metal catalyzed cycloaddition reaction at the carbon-carbon triple bonds of a poly(phenylene ethynylene) polymer. The GNRs can be used in devices such a microelectronic devices.

22 Claims, 10 Drawing Sheets

(51) Int. Cl.
*H01L 31/18* (2006.01)
*B82Y 30/00* (2011.01)
*B82Y 40/00* (2011.01)
*H01L 51/00* (2006.01)
*C01B 31/04* (2006.01)
*C08G 61/02* (2006.01)
*C08G 61/10* (2006.01)
*H01B 1/04* (2006.01)
*B82Y 10/00* (2011.01)
*C07C 15/20* (2006.01)
*H01L 21/02* (2006.01)
*H01L 29/16* (2006.01)

(52) U.S. Cl.
CPC .... *C01B 2204/06* (2013.01); *C01B 2204/065* (2013.01); *C08G 2261/148* (2013.01); *C08G 2261/3422* (2013.01); *C08G 2261/72* (2013.01); *C08G 2261/91* (2013.01); *C08G 2261/92* (2013.01); *C08G 2261/95* (2013.01); *H01L 21/0262* (2013.01); *H01L 21/02527* (2013.01); *H01L 29/1606* (2013.01); *Y02E 10/52* (2013.01); *Y02E 10/549* (2013.01); *Y10S 977/734* (2013.01); *Y10S 977/842* (2013.01); *Y10S 977/932* (2013.01); *Y10T 428/2982* (2015.01)

(56) References Cited

U.S. PATENT DOCUMENTS

2010/0047154 A1 2/2010 Lee et al.
2010/0105834 A1 4/2010 Tour et al.

OTHER PUBLICATIONS

Jiao et al., Narrow graphene nanoribbons from carbon nanotubes, Nature, vol. 458, Apr. 2009, 877-880.*
Kan et al., Chapter 16: Graphene Nanoribbons: Geometric, Electronic, and Magnetic Properties, Physics and Applications of Graphene—Theory, Mar. 2011. ISBN: 978-953-307-152-7.*
Dossel et al., Graphene Nanoribbons by Chemists: Nanometer-Sized, Soluble and Defect-Free, Angew. Chem. Int. Ed. 2011, 50, 2540-2543.*
Dichtel, Reports: DNI7: Bottom-up Synthesis of strutcureally precise graphne nanoribbons (58th Annual Report on Reseach 2013—under sponsorship of the ACS Petroleum Research Fund).*
Yang, X., et al., Two-Dimensional Graphene Nanoribbons, J. Am. Chem. Soc., Mar. 7, 2008, vol. 130, pp. 4216-4217.

* cited by examiner

US 9,556,085 B2

GRAPHENE NANORIBBONS DERIVED FROM POLY(PHENYLENE ETHYNYLENE) POLYMER, METHODS OF MAKING SAME, AND USES THEREOF

CROSS-REFERENCE TO RELATED APPLICATIONS

This application claims priority to U.S. provisional patent application No. 61/479,998, filed Apr. 28, 2011, the disclosure of which is incorporated herein by reference.

STATEMENT REGARDING FEDERALLY SPONSORED RESEARCH

This invention was made with government support from the National Science Foundation under contract no. CHE-1124574. The government has certain rights in the invention.

FIELD OF THE INVENTION

The present invention generally relates to graphene nanoribbons (GNRs) and methods of making GNRs. More particularly, the present invention relates to methods of making GNRs using a metal-catalyzed cycloaddition reaction to arylannulate the carbon-carbon triple bonds of a poly(phenylene ethylene) polymer.

BACKGROUND OF THE INVENTION

Graphene nanoribbons, which are narrow strips of single-layer graphene, are one of the most promising alternatives to silicon in MOSFETs. However, two-dimensional (2D) graphene is a semimetal with no inherent bandgap. Opening a bandgap in graphene in a practical way is one of the most important milestones for the future of nanoelectronics. One approach to do so involves narrowing large-area graphene to create nanoribbons (GNRs) of width <10 nm, which provides band gaps in the range of 1 eV.

The potential of GNRs remains unrealized because of synthetic limitations. Top-down subtractive patterning approaches have been demonstrated to produce GNRs from large area graphene, graphite, or carbon nanotubes. A variety of patterning techniques, including subtractive lithography, electron beam lithography, the use of nanowire etch masks, chemical etching of graphene, chemical vapor deposition, sonicating graphite or graphene, spatially resolved reduction of graphene oxide, and unzipping carbon nanotubes produce GNRs, but do not simultaneously control the width, edge structure, or pendant functionality of the ribbons. These methods all fail to control the atomic structure of the edges of the GNRs, particularly in ribbons <10 nm wide. Methods to form GNRs by oxidatively "unzipping" single-wall or multiwall carbon nanotubes have been previously reported. However, solution-based oxidative unzipping strategies produce insulating graphene oxide ribbons that show inferior conductivity when reduced back to GNRs.

Bottom-up syntheses have produced impractically short ribbons thus far. Two approaches have been demonstrated to-date. Polymerized bis(anthracene) monomers that were sublimed onto crystalline metal surfaces into perfect GNR structures have been previously reported. This method requires formation of the GNRs on the metal surfaces. These GNRs are produced in minute quantities as insoluble sub-monolayers and are unlikely to be relevant for nanoelectronic devices. Bulk synthesis of GNRs from linear polymer precursors has also been reported. A linear polymer is prepared, which is oxidized to form the ribbon's remaining carbon-carbon bonds. The major disadvantage of this approach is that the polymers are quite sterically hindered and high molecular weight samples were not obtained. Thus, the ribbons are 2.7 nm wide (including alkyl groups) but are only an average of 9.2 nm long. The inability to obtain higher molecular weight polymers combined with the difficulty of elaborating the polymer structure severely limit the utility of this approach.

BRIEF SUMMARY OF THE INVENTION

The present invention provides GNRs having a range of sizes. The GNRs have a well-defined edge structure. The GNRs can have a variety of functional groups as end groups. The GNRs can have desirable physical and electrical properties.

The present invention also provides methods of making GNRs. The methods can provide GNRs having controlled lengths, widths, and edge compositions. For example, by using selected precursors and appropriate reaction conditions GNRs having a desired length, width, and edge composition can be formed.

The methods of the present invention can provide predictable control over GNR parameters (e.g., length, width, and edge composition) at the onset of synthesis, ultimately allowing for rationally designing aspects of the GNR structure. The methods of the present invention also can provide macroscopic quantities of structurally precise materials. The methods employ a cycloaddition reaction at carbon-carbon triple bonds of an appropriately substituted poly(phenylene ethynylene) (PPE). The methods provide a means to synthesize high value-added GNR materials from simple petrochemicals.

In an embodiment, the method for making GNRs comprises the steps of contacting a poly(phenylene ethynylene) polymer, an annulating compound, and a catalyst system, such that the PPE polymer or random copolymer is arylannulated, and oxidizing the arylannulated PPE polymer, such that a graphene nanoribbon is formed. The annulation reaction can provide a arylannulated PPE polymer where all of the carbon-carbon triple bonds have been annulated.

GNRs are targets of interest to the semiconductor industry and have applications in nanoelectronic devices and chemical and biological sensors. For example, the GNRs can be used in devices used in these applications.

DETAILED DESCRIPTION OF THE INVENTION

Figure 1:
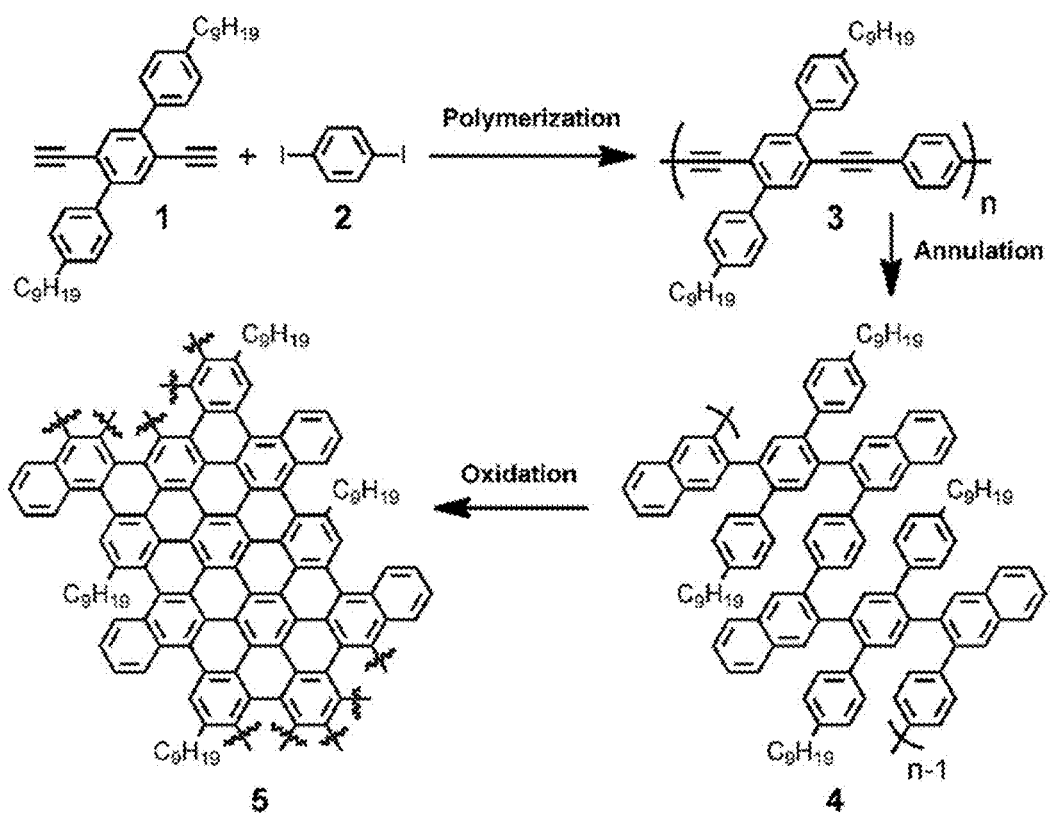
FIG. 1. Example of bottom-up synthesis of structurally precise GNRs from a poly(phenylene ethynylene) precursor.

The present invention provides graphene nanoribbons and methods of making graphene nanoribbons. Also, uses of the graphene nanoribbons (e.g., uses in devices) are provided.

The methods of the present invention can provide control over GNR parameters (e.g., length, width, and edge composition) at the onset of synthesis, ultimately allowing for rationally designing aspects of the GNR structure. Instead of employing subtractive, top-down approaches to pattern GNRs from larger species like graphite, large sheets of graphene and nanotubes, structurally precise GNRs with pre-specified properties are directly and precisely synthesized by the methods disclosed herein. The methods of the present invention can provide macroscopic quantities of structurally precise materials.

The methods disclosed herein are scalable and versatile (e.g., in terms of size and edge functionality control) approaches to prepare GNRs from easily synthesized conjugated polymers. These methods employ an cycloaddition reaction at carbon-carbon triple bonds of an appropriately substituted poly(phenylene ethynylene) (PPE). The resulting polyphenylene is subsequently planarized to the corresponding GNR using oxidative carbon-carbon bond forming chemistry. The methods provide a means to synthesize high value-added GNR materials from simple petrochemicals.

In an aspect, the present invention provides GNRs. The GNRs can have a range of sizes. For example, the GNRs can have a length of from 5 to 600 nm, including all values to the nm and ranges therebetween. In various embodiments, the GNRs have a length of at least 15 nm, at least 20 nm, at least 25 nm, at least 50 nm, or least 100 nm. For example, the GNRs can have a width of 1.2 to 2.0 nm (not including any edge functional groups), including all values to the nm and ranges therebetween. The GNRs have a well-defined edge structure. By "well-defined edge structure" it is meant that the GNRs have end groups that are predictably substituted on the graphene structure (based on the starting materials). The GNRs can have a variety of functional groups as end groups. The end groups are substituents on peripheral (e.g., terminal) aryl rings of the GNRs. For example, the end groups can be hydrogen, alkyl, aryl, ether (e.g., poly(ethylene glycol) groups), thioether, ester, carboxylic acid, amide, halide, azide, or other functional groups. For example, the edge functional groups can controlled by appropriate choice of a 4-substituted benzeneboronic acid for the preparation of the 4,4'-disubstitued 2',5'-diethynyl-1,1':4',1''-terphenyl compound (e.g., S4) that is used to make a PPE. The GNRs can be terminated by the same functional groups as described above for edge functional groups.

The GNRs have desirable physical properties. For example, GNRs can be dispersible in a wide range of solvents. For example, the GNRs can exhibit solubility in solvents such as water, dimethylformamide (DMF), dimethylacetamide (DMAc), N-methylpyrollidone (NMP), chlorinated solvents (e.g., dichlorobenzene, chloroform, and dichloromethane), acetone, tetrahydrofuran (THF), and carbon disulfide (CS$_2$).

Examples of GNRs structures are provided in the following structures:

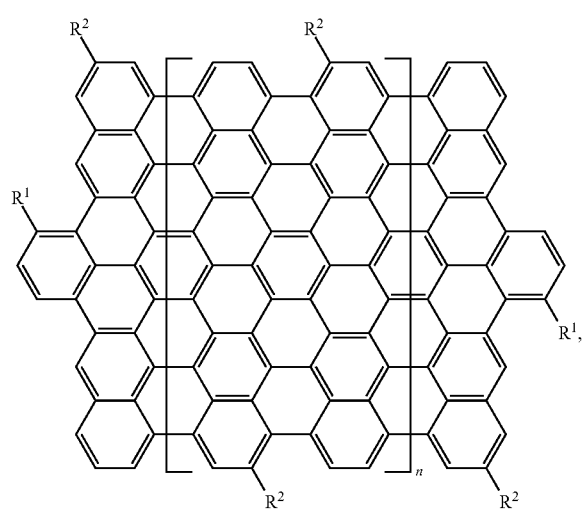

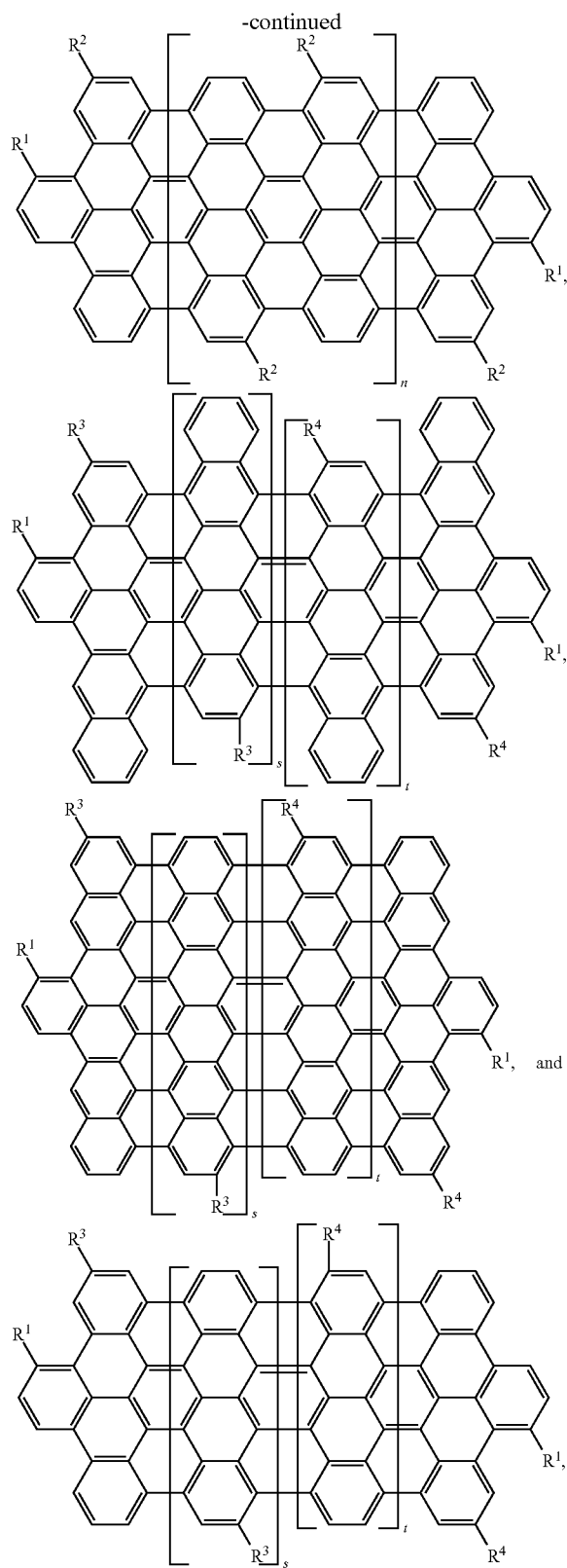

where $R^1$, $R^2$, $R^3$, $R^4$, n, s, and t are as defined herein.

In an aspect, the present invention provides methods of making GNRs. The methods are based on the surprising result that a poly(phenylene ethynylene) polymer can be arylannulated (e.g., benzannulated) where defects in the resulting polyphenylene polymer (e.g., naphthyl ketone defects, unreacted alkyne groups, or phenanthracenes) are minimized or undetectable. In an embodiment, the present invention provides a GNR made by a method disclosed herein.

The methods can provide GNRs having controlled lengths, widths, and edge compositions. For example, by using selected precursors and appropriate reaction conditions (e.g., reaction time, concentration of reactants, and choice of metal catalyst) GNRs having a desired length, width, and edge composition can be formed.

In an embodiment, the method for making a GNR comprises the steps of contacting a poly(phenylene ethynylene) (PPE) polymer, an annulating compound, and a catalyst, such that the PPE polymer is arylannulated (e.g., benzannulated), and oxidizing the arylannulated PPE polymer, such that a graphene nanoribbon is formed.

The term "contacting" as used herein means combining the compounds involved in the reaction so that the desired reaction can take place. The compounds can be combined in a reaction vessel (e.g., a lab scale flask or industrial size reaction vessel). Optionally, the compounds can be combined in a solvent. The solvent can be a mixture of solvents. The solvent can be incorporated in the reaction in a variety of ways. For example, the solvent can be added to the reaction vessel independently and/or one or more of the individual reactants can be dissolved in a solvent prior to combination of the reactants.

PPEs are desirable GNR precursors because of their structural versatility, functional group tolerance, and efficiency of their polymerizations. The PPE can be a homopolymer or a copolymer (e.g., a random copolymer). The PPEs have alternating aryl (e.g., terphenyl) and phenyl groups. For example, the PPEs have at least 10 aryl and 10 phenyl groups. The PPE polymer can have one of the following structures:

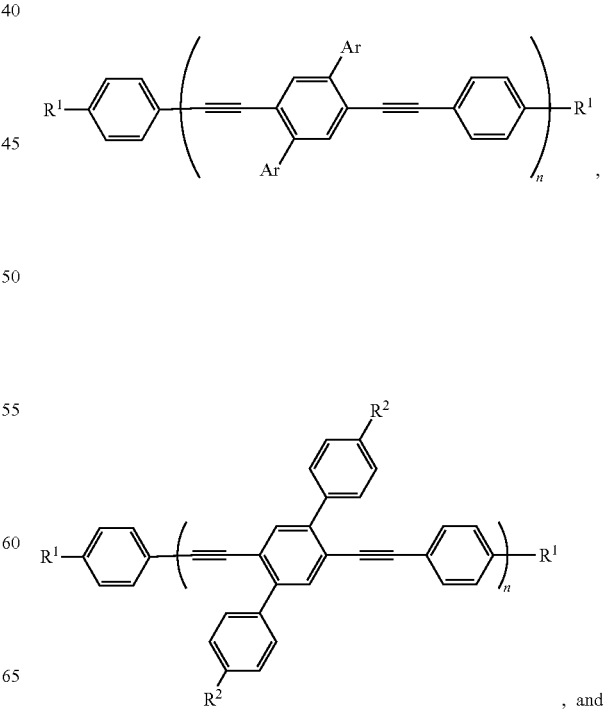

, and

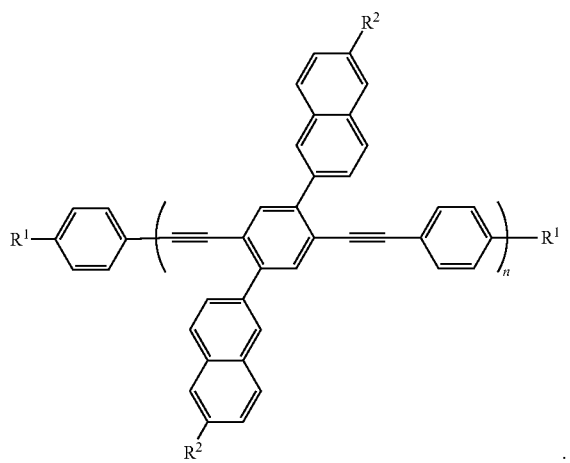

Ar is an aryl group having from 6 carbons to 24 carbons, including all integer number of carbons and ranges therebetween, in the aryl ring(s). Ar can be substituted. Examples of suitable Ar substituents include aryl, ether, thioether, ester, carboxylic acid, amide, halide, azide, and other functional groups as described herein. For example, Ar is

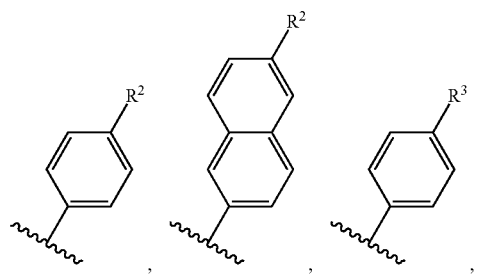

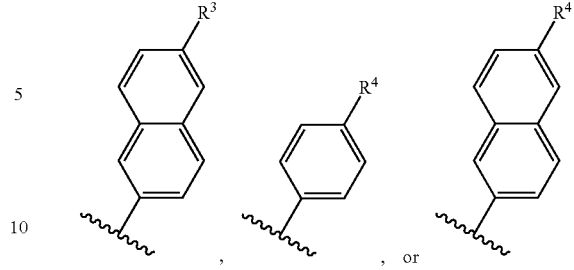

$R^1$, $R^2$, $R^3$, and $R^4$ functional groups are independently selected from the group consisting of H, alkyl, aryl, ether (e.g., polyethylene glycol groups ($-CH_2-CH_2-O-$)$_z$, where z is from 2 to 20), thioether, ester, carboxylic acid, amide, halide, azide, or other functional groups. The alkyl functional group (or an alkyl moiety of one of the functional groups) can have from 1 to 100 carbons, including all integer number of carbons and ranges therebetween. The alkyl functional group (or alkyl moiety) can be unsubstituted or substituted. The alkyl functional group (or alkyl moiety) can be branched or linear. The aryl functional group can have from 6 carbons to 24 carbons, including all integer number of carbons and ranges therebetween, in the aryl ring(s). The alkyl functional group (or alkyl moiety) or aryl functional group can be substituted. Examples of suitable alkyl functional group (or alkyl moiety) or aryl functional group substituents include aryl, ether, thioether, ester, carboxylic acid, amide, halide, azide, and other functional groups. The value of n (degree of polymerization) is from 10 to 500, including all integer values of n and ranges therebetween. The PPE polymers have a molecular weight of from 10,000 to 500,000, including all integer values of g/mol and ranges therebetween. PPE polymers can be synthesized by known methods. PPE polymers can also be synthesized by the methods disclosed herein.

For example, the PPE polymer can be a PPE random copolymer. These copolymers can be used to incorporate multiple edge functional groups in the GNRs. A PPE random copolymer can have one of the following structures:

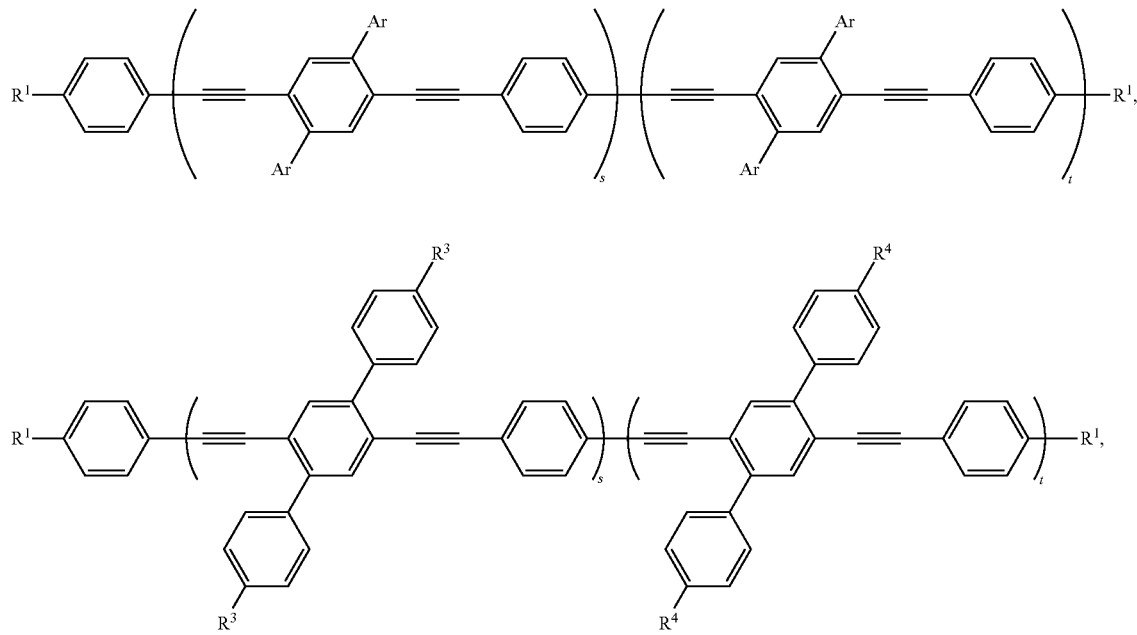

-continued

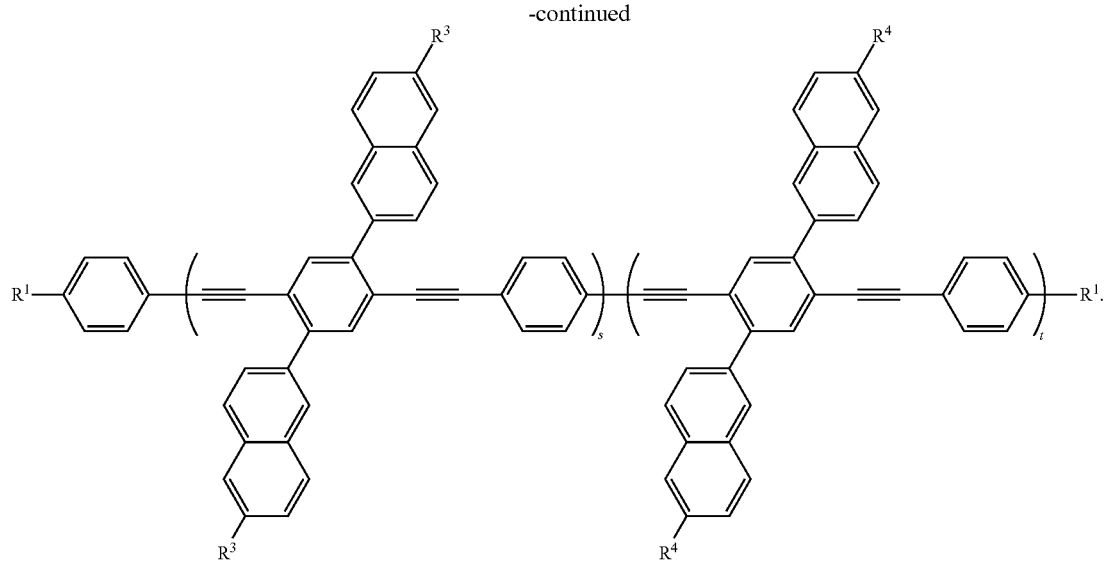

R³ and R⁴ functional groups are individually, at each occurrence in the PPE random copolymer, as described herein. Ar is individually, at each occurrence in the random PPE copolymer, as described above for Ar. The sum of the s and t values are from 10 to 500, including all ranges therebetween. The PPE random copolymers have a molecular weight of from 10,000 to 500,000, including all integer values of g/mol and ranges therebetween. PPE random copolymers can be synthesized by known methods.

The annulating compound has at least an aryl ethynylene group, and an en-al group (i.e., an α, β-unsaturated aldehyde group) or an aryl aldehyde group. The aryl ethynylene group and en-al group are connected at the ethynylene terminus of the aryl ethynylene and the β-position of the en-al. The aryl ethynylene and aryl aldehyde are connected at the ethynylene terminus of the aryl ethynylene and at a position adjacent to the aldehyde of the aryl aldehyde.

The annulating compound can have on of the following structures:

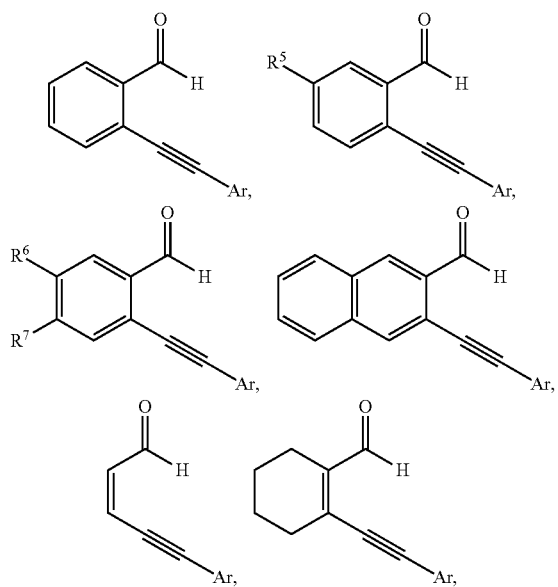

-continued $R^5$, $R^6$, and $R^7$ functional groups can be is H, alkyl, aryl, ether, ester, carboxylic acid, amide, halide, azide, or other functional groups. Ar is as described herein. The alkyl functional group (or an alkyl moiety of one of the functional groups) can be unsubstituted or substituted. The alkyl functional group (or alkyl moiety) can be branched or linear. The aryl functional group can have from 6 carbons to 24 carbons, including all integer number of carbons and ranges therebetween, in the aryl ring(s). The alkyl functional group (or alkyl moiety) can be substituted. Examples of suitable alkyl functional group (or alkyl moiety) or aryl functional group substituents include aryl, ether, thioether, ester, carboxylic acid, amide, halide, azide, and other functional groups.

For example, the annulating compound can be a 2-en-4-yn-al compound. The ene carbons can be substituted to form a 2,3-disubstitued-2-en-4-yn-al compound such that an aryl group is formed. Taken together the carbons at the 2- and 3-positions form part of an aryl ring. For example, the aryl group can be a phenyl group, naphthyl group or anthracenyl group. The aryl groups can be substituted as described herein. For example the annulating compound can have the following structure:

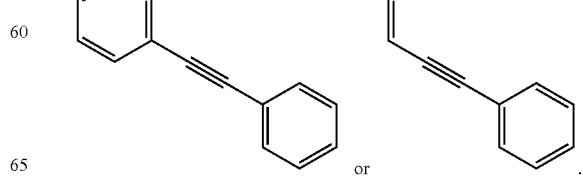

or

By choosing appropriate PPE and annulating compounds, GNRs of desired widths can be formed. For example, the width of the GNRs can be increased in 4 carbon increments (up to a total of 12 carbons) by increasing the size (e.g., adding phenyl rings) of the aryl group of the annulating compound.

The arylannulation reaction results in an intramolecular cycloaddition reaction at carbon-carbon triple bonds in the polymer backbone providing a polyphenylene polymer. In various examples, at least 90%, at least 95%, at least 99% of the carbon-carbon triple bonds undergo the intramolecular cycloaddition reaction. It is desirable that the arylannulated product has no detectable carbon-carbon triple bonds. Carbon-carbon triple bonds can be quantified by methods known in the art. For example, the carbon-carbon triple bonds can be quantified by NMR spectroscopy (e.g., $^{13}C$ NMR) or Infrared or UV/visible spectroscopy. In an embodiment, the arylannulated product has no residual carbon-carbon triple bonds.

For example the arylannulation product can have the following structure:

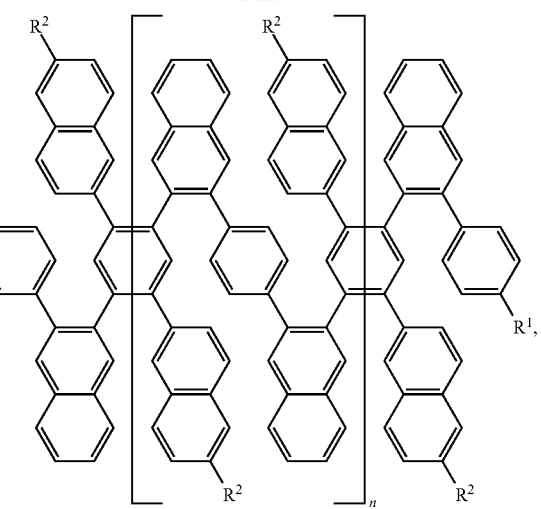

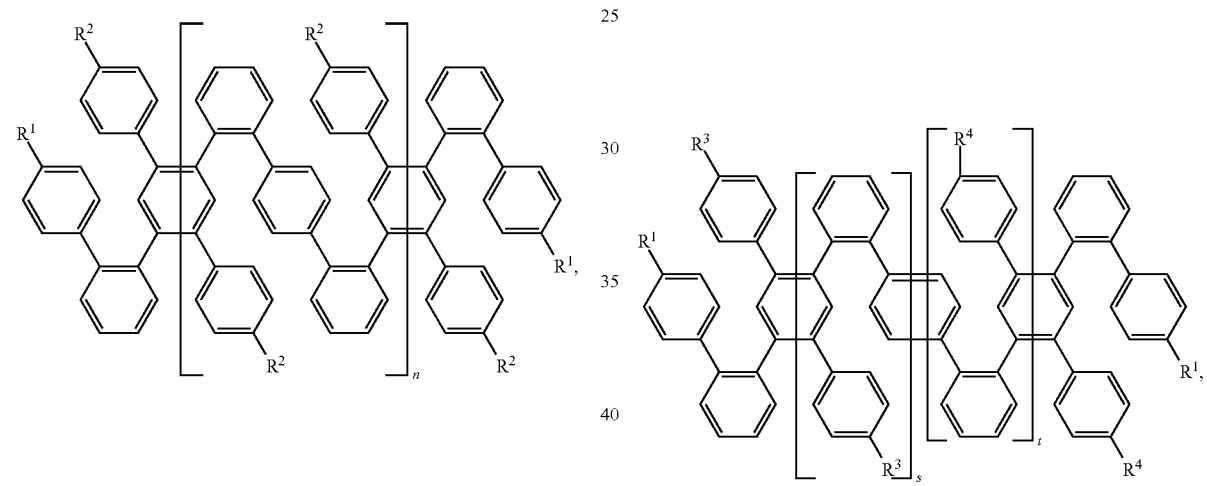

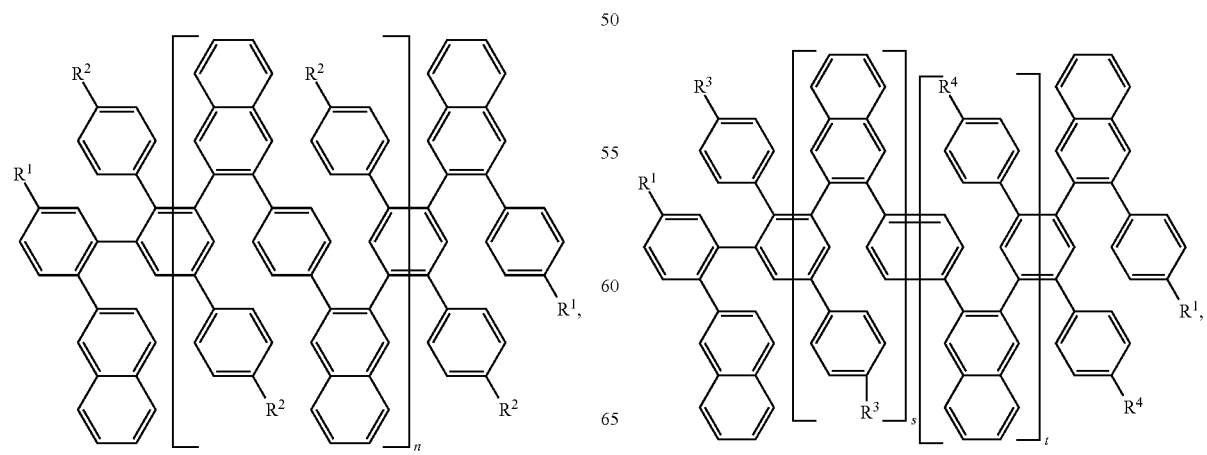

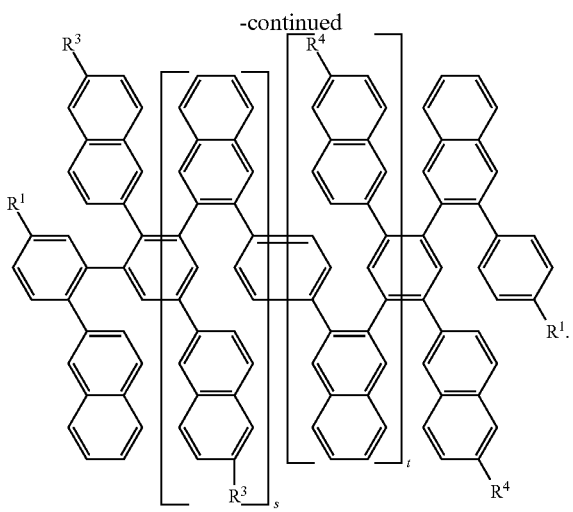

-continued $R^1$, $R^2$, $R^3$, $R^4$, n, s, and t are as described for the PPE polymer. The arylannulated PPE copolymers have a molecular weight of from 10,000 to 500,000, including all integer values of g/mol and ranges therebetween. PPE random copolymers can be synthesized by known methods.

The catalyst system includes a metal salt and a Bronsted acid (i.e., a protic acid). The catalyst system affects arylannulation of the PPE polymer. The metal salt can be a copper(II) salt or a zinc(II) salt. Examples of suitable copper (II) salts include $Cu(OTf)_2$ (OTf is triflate), $Cu(acetate)_2$, $Cu(TFA)_2$ (TFA is trifluoroacetate), $Cu(halide)_2$ (halides are $F^-$, $Cl^-$, $Br^-$, $I^-$), $Cu(sulfate)_2$, and Cu(II) oxide. Examples of suitable zinc (II) salts include $Zn(OTf)_2$ (OTf is triflate), $Zn(acetate)_2$, $Zn(TFA)_2$ (TFA is trifluoroacetate), $Zn(halide)_2$ (halides are $F^-$, $Cl^-$, $Br^-$, $I^-$), $Zn(sulfate)_2$, and Zn oxide.

A variety of protic acids should be used. The protic acid should have an acidity equivalent to or greater than that of acetic acid. The acid should be soluble in the solvent used in the annulation reaction. Examples of suitable protic acids include acetic acid, trifluoroacetic acid, difluoroacetic acid, monofluoroacetic acid, trichloroacetic acid, dichloroacetic acid, monochloroacetic acid, p-toluenesuflonic acid, and hydrogen chloride.

The PPE polymer, annulating compound, and catalyst can be contacted in a solvent. Suitable solvents include chlorinated solvents (e.g., chlorinated hydrocarbons such as chloroform and methylene chloride), THF, acetonitrile, and DMF.

Determination of conditions (e.g., concentrations of PPE polymer, annulating compound, and catalyst, and reaction temperature) to affect a desired level of arylannulation are within the purview of one having skill in the art. The polymer should be soluble in the solvent used in the annulation reaction. For example, the arylannulation reaction can be run at temperatures of from 60 to 150° C., including all values to the ° C. and ranges therebetween. The reaction can be run at temperatures above the boiling point of a solvent using a sealed reaction vessel. It is desirable to run the reaction in an inert atmosphere (e.g., in a $N_2$ or Argon atmosphere).

The arylannulated PPE can be isolated, and, optionally, purified, and then oxidized (e.g., in a separate reaction vessel). The arylannulated PPE can be isolated or purified by methods known in the art. For example, the arylannulated PPE can be isolated or purified as described herein.

Oxidation of the resulting polyphenylene polymer or copolymer forms the carbon-carbon bonds necessary to planarize the annulated PPE polymer into a graphitic ribbon (i.e., a GNR). The arylannulated PPE can be oxidized by methods known in the art. For example, the arylannulated PPE can be oxidized by contacting the arylannulated PPE with an oxidant (e.g., under Sholl oxidation conditions). A variety of suitable oxidants are known in the art. Examples of suitable oxidants include $FeCl_3$, (2,3-Dichloro-5,6-dicyano-1,4-benzoquinone) DDQ (which is used with a protic source), and manganese dioxide). The arylannulated PPE and oxidant can be contacted in a solution. A mixture of solvents can be used. Suitable solvents include chlorinated solvents (e.g., methylene chloride, chloroform, dichloroethane, tetrachloroethylene, dichlorobenzene), and nitromethane.

The oxidized product (GNRs) can be isolated and/or purified. The GNRs can be isolated or purified by methods known in the art. For example, the GNRs can be isolated or purified as described herein.

Determination of conditions (e.g., concentrations of arylannulated PPE polymer and oxidant, and reaction temperature) to affect the desired level of oxidation are within the purview of one having skill in the art. It is desirable that the concentration of arylannulated polymer be 50 mM or less. The reaction can be run at a variety of temperatures. For example, the reaction can be run at room temperature (e.g., 20 to 25° C. depending on the local environment) or at temperatures lower than room temperature. For example, the oxidation of the arylannulated PPE can be carried out by contacting the arylannulated PPE with $FeCl_3$ in a mixture of $CH_2Cl_2$ and nitromethane at room temperature. It is desirable to run the reaction in an inert atmosphere (e.g., in a $N_2$ or Argon atmosphere).

The GNRs are dispersible in organic solvents as described herein. The GNRs also exhibit vibrational signatures (e.g., Raman spectral bands) that are consistent with a graphene structure. For example, the GNRs exhibit Raman spectral bands at frequencies corresponding to the D-band, G-band, 2*D-band, 2*G-band, and D-band+G-band vibrational modes.

In an aspect, the present invention provides a device comprising a graphene nanoribbon (or graphene nanoribbons) of the present invention. Graphene nanoribbons are targets of interest to the semiconductor industry and have applications in nanoelectronic devices and chemical and biological sensors. For example, GNRs can be used as conductors in, for example, transistors, solar cells, and light emitting diodes (LEDs). Such devices can be fabricated by methods known in the art. For example, the device can be transistors, solar cells, LEDs, and chemical and biological sensors.

The following examples are presented to illustrate the present invention. They are not intended to limiting in any manner.

Example 1

An example of GNR preparation by a method of the present invention.

Materials. All reagents were purchased from commercial sources and used without further purification. $CH_2Cl_2$, PhMe, and MeOH were purchased from commercial sources and purified using a custom-built alumina-column based solvent purification system. Other solvents were purchased from commercial sources and used without further purification Instrumentation. Infrared spectra were recorded on a Thermo Nicolet iS10 with a diamond ATR attachment and are uncorrected. Ultraviolet/visible/near infrared absorbance spectra were recorded on a Cary 5000 spectrophotometer with a Hg lamp. A quartz cuvette rated for transparency in the near infrared region containing the pure solvent of interest for the measurement was used for background correction.

Photoemission and excitation spectra were recorded on a Horiba Jobin Yvon Fluorolog-3 fluorescence spectrophotometer equipped with a 450 W Xe lamp, double excitation and double emission monochromators, a digital photon-counting photomultiplier and a secondary InGaAs detector for the NIR range. Correction for variations in lamp intensity over time and wavelength was achieved with a solid-state silicon photodiode as the reference. The spectra were further corrected for variations in photomultiplier response over wavelength and for the path difference between the sample and the reference by multiplication with emission correction curves generated on the instrument.

Raman spectra were recorded on a Renishaw InVia confocal raman microscope with excitation wavelength at 488 nm. Samples were drop-cast on Si wafers.

Thermogravimetric analysis from 20-600° C. was carried out on a TA Instruments Q500 Thermogravimetric Analyzer in a $N_2$ atmosphere using a 10° C./min ramp without equilibration delay.

Mass spectra were obtained on a Waters MALDI micro MX MALDI-TOF mass spectrometer using positive ionization and a reflectron detector. MALDI samples were prepared by depositing the analyte dissolved in a saturated dithranol solution onto a stainless steel sample plate. The plate was dried in air before loading it into the instrument.

NMR spectra were recorded on a Varian 400 MHz or Bruker ARX 300 MHz spectrometer using a standard $^1$H/X Z-PFG probe at ambient temperature with a 20 Hz sample spin rate.

Size exclusion chromatography (SEC) was performed on two 7.5-μm columns (PolyPore, Varian, Inc.) connected in series. Tetrahydrofuran was used as the mobile phase at 1.0 mL/min flow from a Shimadzu LC-20AD isocratic pump. The detector system consisted of a miniDawn three angle, light-scattering system, followed downstream by an Optilab Rex differential refractometer from Wyatt Technologies.

Transmission electron microscopy was performed on a PEI Technai T12 Spirit operating at 120 kV. Samples were spotted from dilute solutions of 1,2-$C_6H_4Cl_2$ using a nebulizer on to 400 mesh Cu grids precoated with a ~3 nm holey carbon film.

Atomic force microscopy was performed on a Veeco Dimension 3100 in tapping mode using a silicon AFM probe (Tap190DLC, Budget Sensors). Samples were spotted on freshly cleaved highly ordered pyrolytic graphite (HOPG) surfaces.

1,4-dibromo-2,5-diiodobenzene S1: S1 was synthesized using known methods. Its $^1$H and $^{13}$C NMR spectra were consistent with previously reported data.

Synthesis of 1,4-dibromo-2,5-bis(trimethylsilylethynyl)benzene S2: Anhydrous PhMe (30 mL) and freshly distilled diisopropylamine (15 mL) were added to a 100 mL flask and sparged with $N_2$ for 20 min. 1,4-dibromo-2,5-diiodobenzene (3.000 g, 6.15 mmol), TMS-acetylene (1.510 g, 15.38 mmol), $Pd(PPh_3)_2Cl_2$ (216 mg, 0.308 mmol) and CuI (117 mg, 0.615 mmol) were added to the solution, in sequence. The mixture was stirred at rt for 20 h. The crude reaction mixture was filtered through celite and washed with additional $CH_2Cl_2$ (400 mL). Evaporation of the solvent provided the crude product as a solid, which was purified by chromatography ($SiO_2$, hexanes) followed by recrystallization from DMSO to give S2 (1.801 g, 69% yield) as white needles. $^1$H and $^{13}$C NMR spectroscopy were consistent with previous reports.

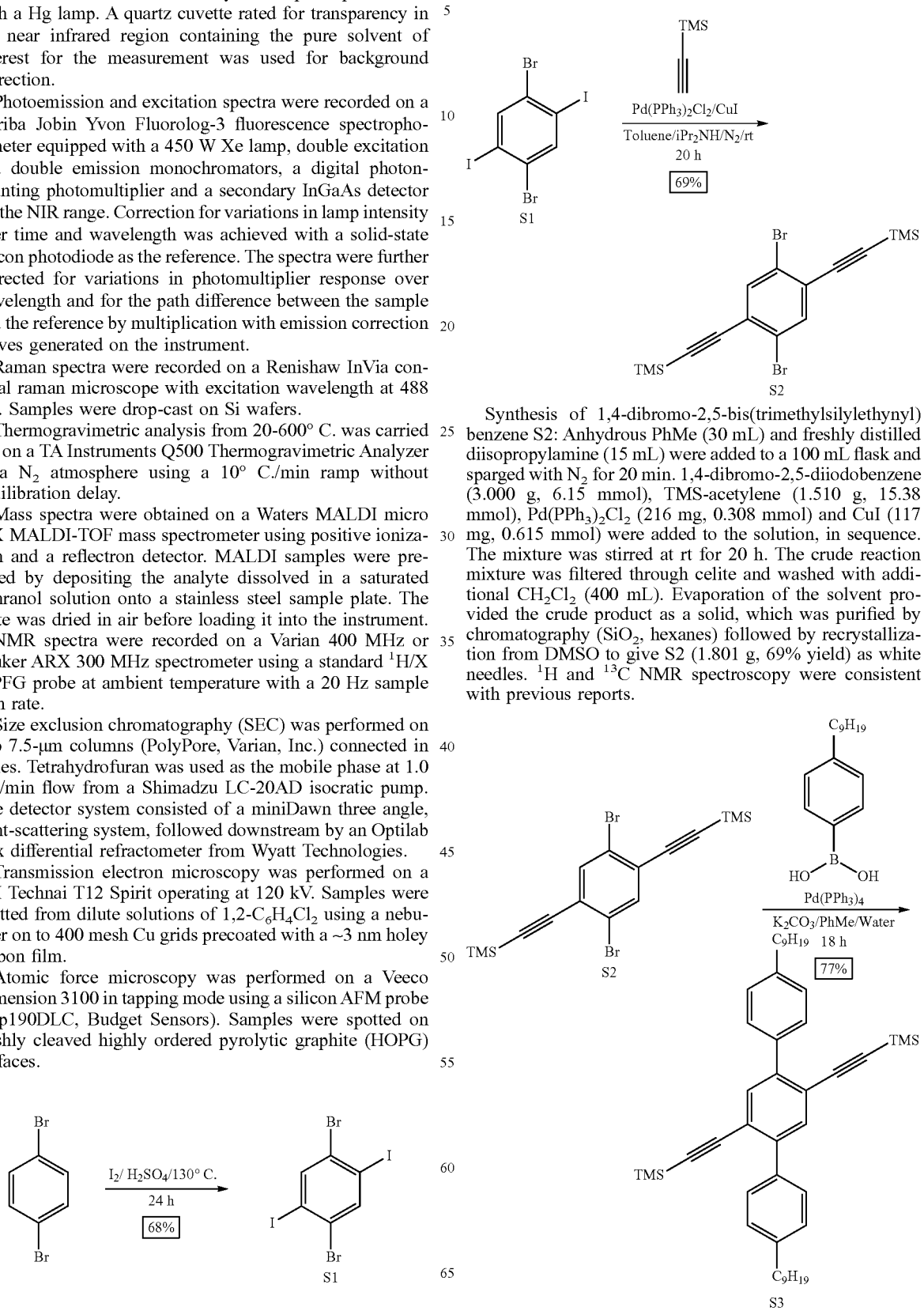

Synthesis of S3: S2 (0.650 g, 1.518 mmol), 4-n-nonyl-benzeneboronic acid (0.829 g, 3.339 mmol), K$_2$CO$_3$ (0.629 g, 4.553 mmol), Pd(PPh$_3$)$_4$ (0.175 g, 0.152 mmol) were dissolved in a mixture of PhMe (15 mL) and water (3 mL), subjected to three freeze-pump-thaw cycles and backfilled with a N$_2$ atmosphere. The mixture was heated to 100° C. for 18 h. The solution was cooled to rt, filtered through celite, and washed with additional CH$_2$Cl$_2$ (250 mL). The solvent was evaporated and the resulting oil was purified by chromatography (SiO$_2$, hexanes to 1% v/v EtOAc/hexanes) to give S3 (0.786 g, 77% yield) as a yellow oil that solidified slowly. S3: $^1$H NMR (400 MHz, CDCl$_3$) δ 7.59 (s, 2H), 7.55 (d, J=7.8 Hz, 4H), 7.24 (d, J=7.8 Hz, 4H), 2.68 (t, J=7.8 Hz, 4H), 1.68 (m, 4H), 1.39-1.25 (m, 24H), 0.95-0.91 (m, 6H), 0.18 (s, 18H). $^{13}$C NMR (100 MHz, CDCl$_3$) δ 142.81, 142.73, 136.75, 134.49, 129.49, 128.27, 121.95, 104.98, 99.54, 36.12, 32.31, 31.94, 30.12, 30.00, 29.77, 29.67, 23.09, 14.53, 0.42. IR (solid, ATR) 2956, 2923, 2853, 2155, 1521, 1479, 1376, 1248, 1187, 1017, 906, 863, 839, 758, 722, 699 cm$^{-1}$. HRMS (EI) calcd for [C$_{46}$H$_{66}$Si$_2$]$^+$ 674.4703. found 674.4706.

Synthesis of S4: K$_2$CO$_3$ (2.87 g, 20.7 mmol) was suspended in MeOH (41 mL) and a solution of S3 (1.400 g, 2.073 mmol) dissolved in CH$_2$Cl$_2$ (10 mL) was added. The mixture was stirred at 45° C. for 2 h, after which it was cooled to rt and poured into aqueous HCl (2M, 10 mL). The solution was washed with Et$_2$O (3×50 mL), and the combined organic layers were washed with brine (20 mL), dried (MgSO$_4$) and filtered. The solvent was evaporated to give S4 (1.060 g, 96% yield) as a white solid that was used without further purification. S4: $^1$H NMR (300 MHz, CDCl$_3$) δ 7.63 (s, 2H), 7.55 (d, J=8.0 Hz, 4H), 7.25 (d, J=8.0 Hz, 4H), 3.14 (s, 2H), 2.66 (t, J=7.6 Hz, 4H), 1.67 (m, 4H), 1.40-1.25 (m, 24H), 0.91-0.87 (m, 6H). $^{13}$C NMR (75 MHz, CDCl$_3$) δ 142.89, 142.71, 136.33, 135.11, 129.11, 128.30, 121.07, 82.91, 81.74, 35.92, 32.06, 31.54, 29.72, 29.69, 29.59, 29.50, 22.84, 14.28. IR (solid, ATR) 3287, 2953, 2918, 2851, 1522, 1480, 1468, 1414, 1376, 1265, 1139, 1018, 902, 841, 823, 721, 666 cm$^{-1}$. HRMS (EI) calcd for [C$_{40}$H$_{50}$]$^+$ 530.3913. found 530.3896.

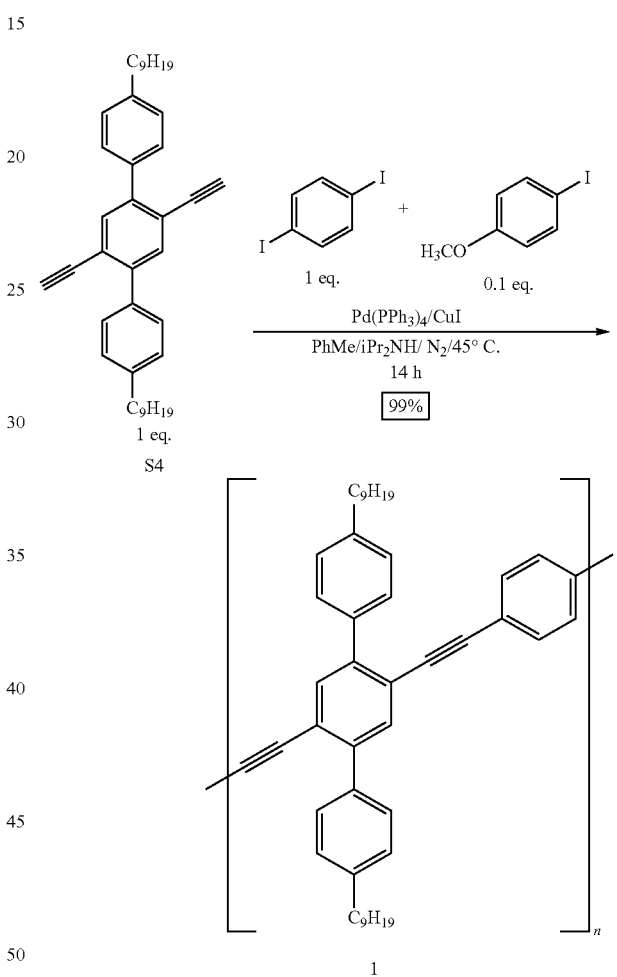

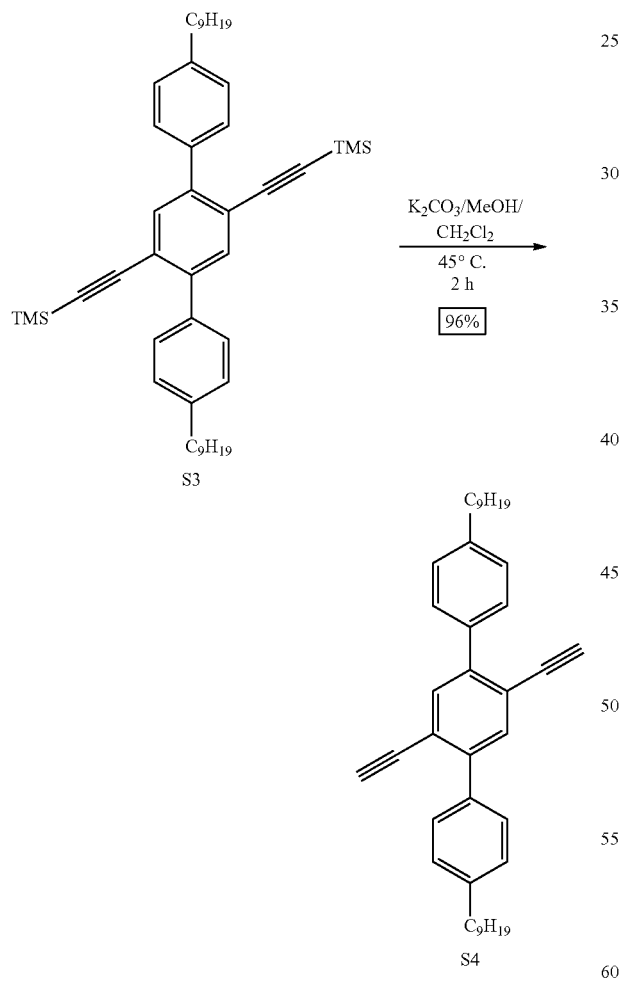

Synthesis of polymer 1: S4 (0.200 g, 0.377 mmol), 1,4-diiodobenzene (0.125 g, 0.377 mmol) and 4-iodoanisole (0.009 g, 0.04 mmol) were dissolved in anhydrous PhMe (12 mL) and freshly distilled diisopropylamine (4 mL). The solution was subjected to three freeze-pump-thaw cycles and backfilled with N$_2$. While the solution was frozen, Pd(PPh$_3$)$_4$ (22 mg, 0.019 mmol) and CuI (7 mg, 0.038 mmol) were added under positive N$_2$ pressure. After another freeze-pump-thaw cycle, the flask was filled with N$_2$ and heated to 45° C. After 14 h at 45° C., the solution was cooled to rt and poured into a saturated aqueous NH$_4$Cl solution (100 mL). The aqueous solution was washed with CH$_2$Cl$_2$ (3×50 mL). The combined organic layers, including some undissolved polymer were concentrated to a total volume of 3 mL and were precipitated into vigorously stirred MeOH (500 mL). The precipitate was collected by filtration and dried under vacuum to give the polymer 1 (227 mg, 99% yield) as a yellow solid. 1: $^1$H NMR (300 MHz, CDCl$_3$) δ 7.70 (s, 2H), 7.63 (d, J=7.8 Hz, 4H), 7.28 (d, J=7.8 Hz, 4H), 7.26 (s, 4H), 2.70 (t, J=7.5 Hz, 4H), 1.70 (m, 4H), 1.44-1.22 (m, 24H), 0.91-0.84 (m, 6H). $^{13}$C NMR (100 MHz, C$_2$D$_2$Cl$_4$) δ 142.93, 142.11, 136.90, 133.98, 131.53, 129.35, 128.29, 121.92, 109.95, 36.18, 32.24, 31.96, 30.05, 30.02, 29.95, 29.80, 23.12, 14.56. IR (solid, ATR) 3046, 2952, 2922, 2852, 1511, 1467, 1379, 1261, 1185, 1099, 1017, 901, 830, 721, 694 cm$^{-1}$.

3 (147 mg, 61% yield) was recovered from the extraction as a brown solid. 3: $^1$H NMR (400 MHz, CDCl$_3$) δ 8.20-5.05 (m, 26H), 2.33 (brs, 4H), 1.65-0.50 (m, 34H). $^{13}$C NMR (75 MHz, CDCl$_3$) δ 141.75-135.77 (br), 133.58 (brs), 131.56-127.05 (br), 124.41 (brs), 35.69, 32.04, 29.51 (brs), 22.82, 14.26. IR (solid, ATR) 3053, 3015, 2924, 2853, 1673, 1596, 1488, 1456, 1370, 1229, 1139, 1017, 950, 891, 833, 746 cm$^{-1}$.

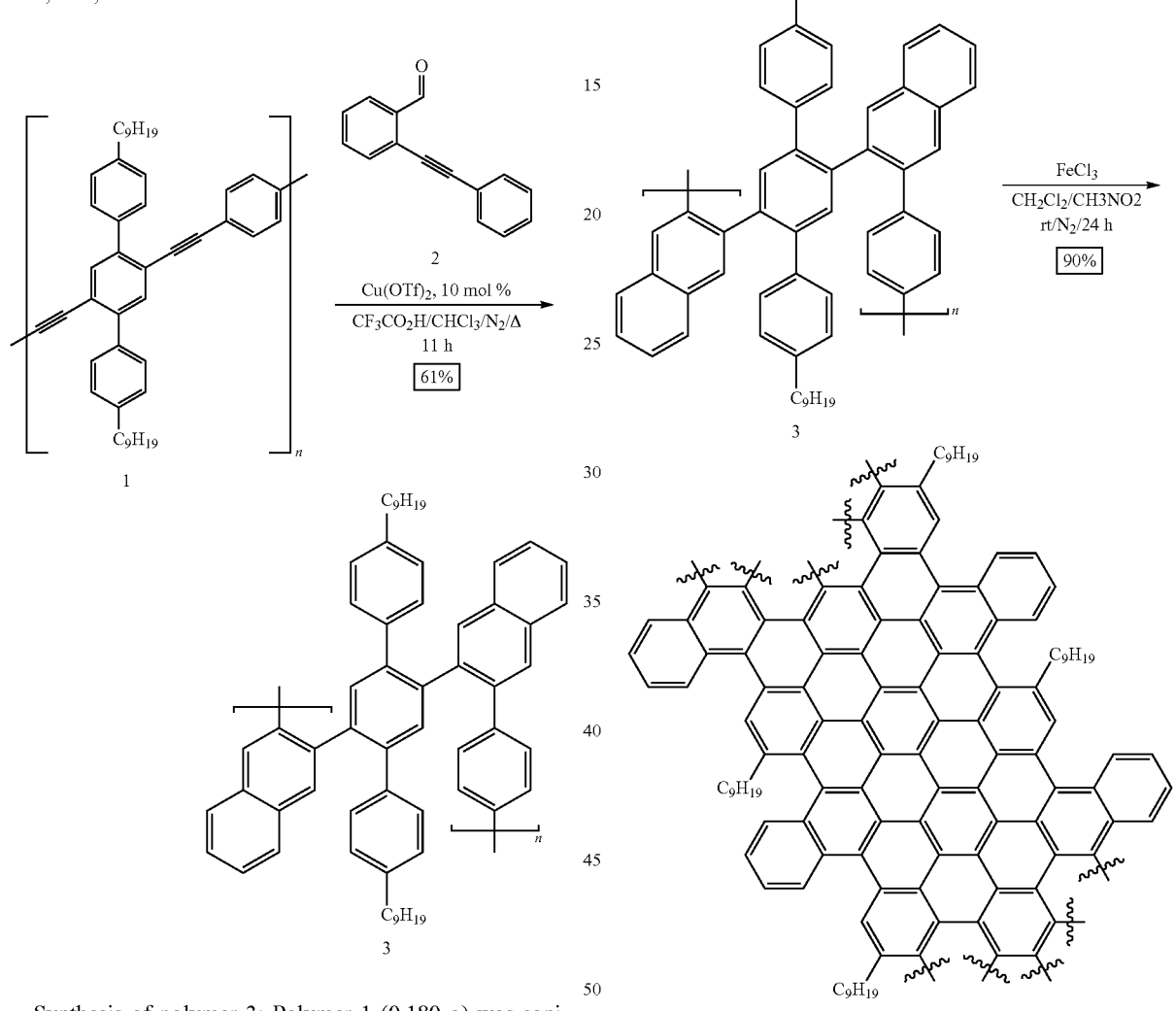

Synthesis of polymer 3: Polymer 1 (0.180 g) was sonicated in CHCl$_3$ (10 mL) until finely dispersed and was heated until the polymer dissolved. The solution was transferred into a 25 mL Schlenk tube and sparged with N$_2$. CU(OTf)$_2$ (11 mg, 0.030 mmol), 2-Phenylethynyl-benzaldehyde 2 (366 mg, 1.779 mmol), and CF$_3$CO$_2$H (0.14 mL, 1.779 mmol) were added under positive N$_2$ pressure. The tube was sealed and heated to 100° C. for 11 h, after which it was cooled to rt. The mixture was poured into a saturated aqueous NaHCO$_3$ solution (75 mL) and was extracted with CH$_2$Cl$_2$ (3×50 mL). The combined organic layers were dried (MgSO$_4$), filtered and the solvent was evaporated. The crude product was dissolved in minimum amount of CH$_2$Cl$_2$ and precipitated into a large excess of vigorously stirring acetone (200 mL). The resulting precipitate was collected by centrifugation and subjected to Soxhlet extraction using acetone as the liquid phase for 24 h. The remaining insoluble powder Synthesis of graphene nanoribbon (GNR) 4: Polymer 3 (0.050 g) was dissolved in CH$_2$Cl$_2$ (40 mL) under an N$_2$ atmosphere. A solution of FeCl$_3$ (0.300 g, 1.849 mmol) dissolved in CH$_3$NO$_2$ (2 mL) was added dropwise under N$_2$. The solution was stirred for 24 h, after which it was poured into MeOH (50 mL), and a black precipitate formed. The precipitate was recovered by centrifugation and was redispersed in MeOH (20 mL) and centrifugated two more times. After the final centrifugation step, the precipitate subjected to Soxhlet extraction using acetone as the liquid phase for 24 h, providing an insoluble fraction that corresponded to graphene nanoribbon 4 (0.044 g, 90% yield) as a black powder. 4: IR (solid, ATR) 2950, 2919, 2850, 1730, 1654, 1463, 1377, 1265, 1118, 1073, 796, 749 cm$^{-1}$.

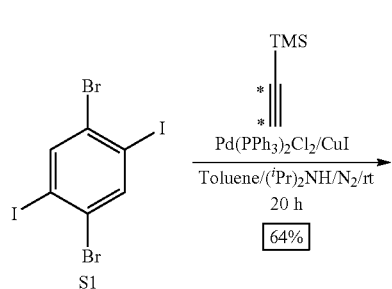

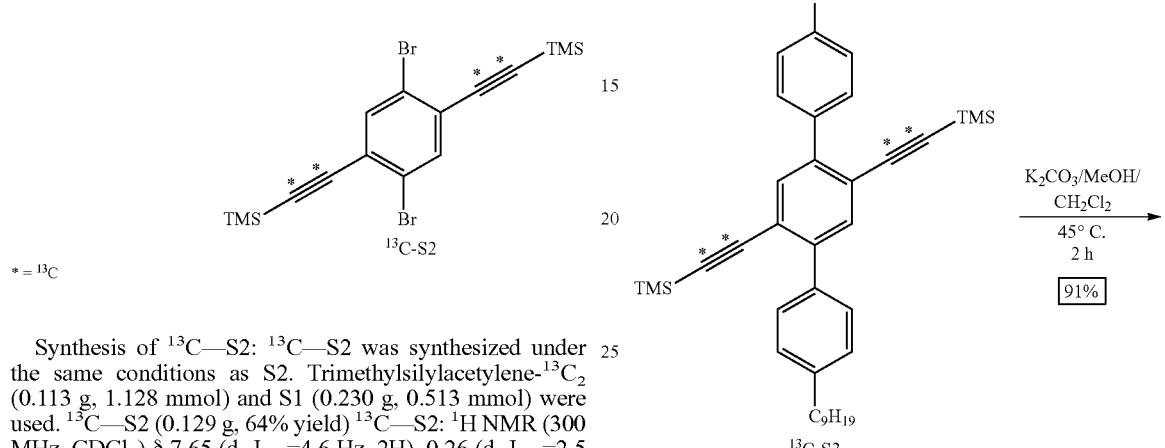

Synthesis of $^{13}$C—S2: $^{13}$C—S2 was synthesized under the same conditions as S2. Trimethylsilylacetylene-$^{13}$C$_2$ (0.113 g, 1.128 mmol) and S1 (0.230 g, 0.513 mmol) were used. $^{13}$C—S2 (0.129 g, 64% yield) $^{13}$C—S2: $^1$H NMR (300 MHz, CDCl$_3$) δ 7.65 (d, J$_{CH}$=4.6 Hz, 2H), 0.26 (d, J$_{CH}$=2.5 Hz, 18H). $^{13}$C NMR (75 MHz, CDCl$_3$) δ 103.4 (d, J$_{CC}$=139.0 Hz), 100.9 (d, J$_{CC}$=139.0 Hz).

Synthesis of $^{13}$C—S3: $^{13}$C—S3 was synthesized under the same conditions as S3. Instead of S2, $^{13}$C—S2 (0.129 g, 0.298 mmol) was used. $^{13}$C—S3 (0.203 g, 99% yield) $^{13}$C—S3: $^1$H NMR (300 MHz, CDCl$_3$) δ 7.60-7.55 (m, 4H), 7.31-7.13 (m, 6H), 2.70-2.56 (m, 4H), 1.71-1.57 (m, 4H), 1.40-1.16 (m, 24H), 0.94-0.86 (m, 6H), 0.15 (d, J$_{CH}$=2.6 Hz, 18H). $^{13}$C NMR (75 MHz, CDCl$_3$) δ 105.1 (d, J$_{CC}$=136.7 Hz), 99.4 (d, J$_{CC}$=136.7 Hz).

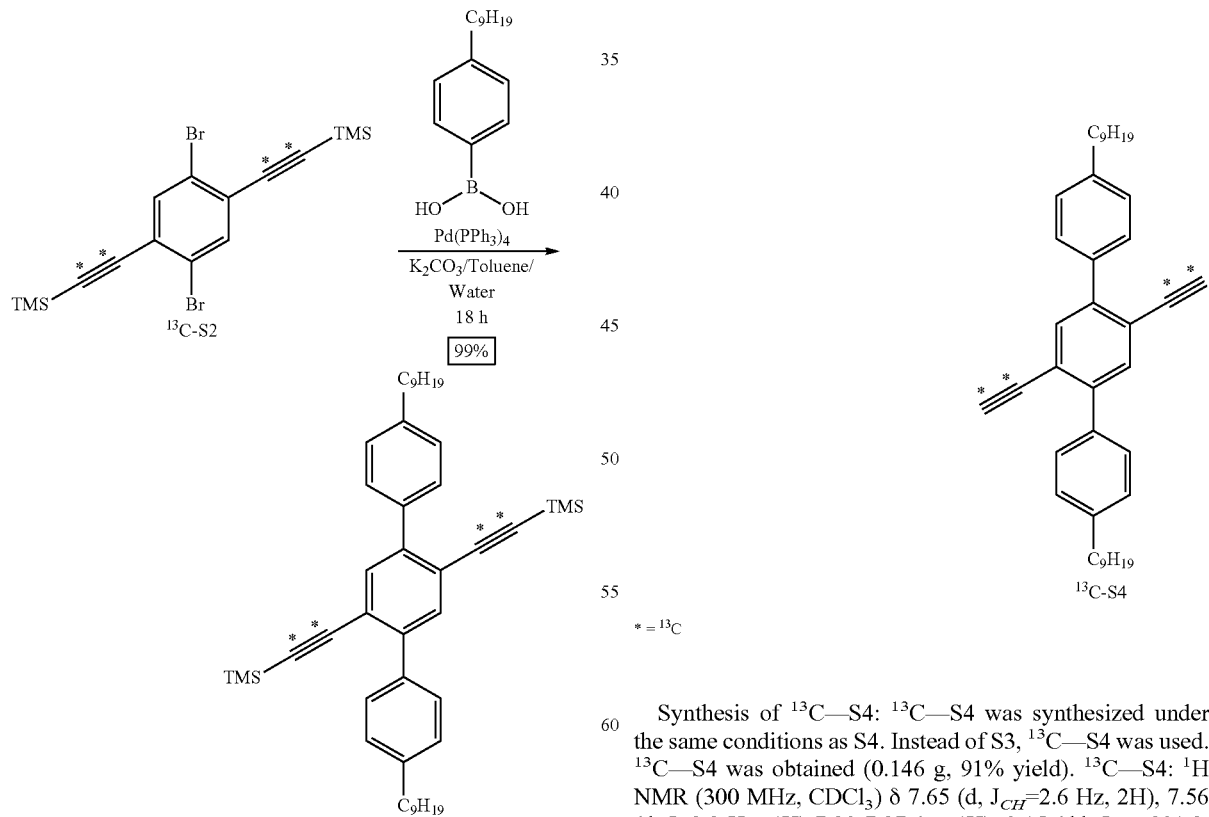

Synthesis of $^{13}$C—S4: $^{13}$C—S4 was synthesized under the same conditions as S4. Instead of S3, $^{13}$C—S4 was used. $^{13}$C—S4 was obtained (0.146 g, 91% yield). $^{13}$C—S4: $^1$H NMR (300 MHz, CDCl$_3$) δ 7.65 (d, J$_{CH}$=2.6 Hz, 2H), 7.56 (d, J=8.2 Hz, 4H) 7.29-7.27 (m, 4H), 3.15 (dd, J$_{CH}$=201.2, 99.3 Hz, 2H) 2.68 (t, J=7.5 Hz, 4H), 1.73-1.63 (m, 4H), 1.45-1.22 (m, 24H), 0.93-0.86 (m, 6H). $^{13}$C NMR (75 MHz, CDCl$_3$) δ 82.9 (d, J$_{CC}$=177.8 Hz), 80.8 (d, J$_{CC}$=177.8 Hz).

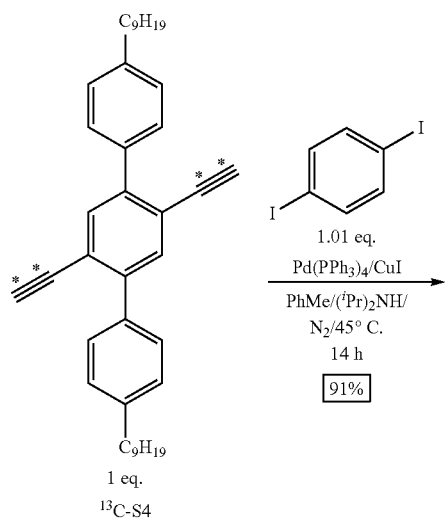

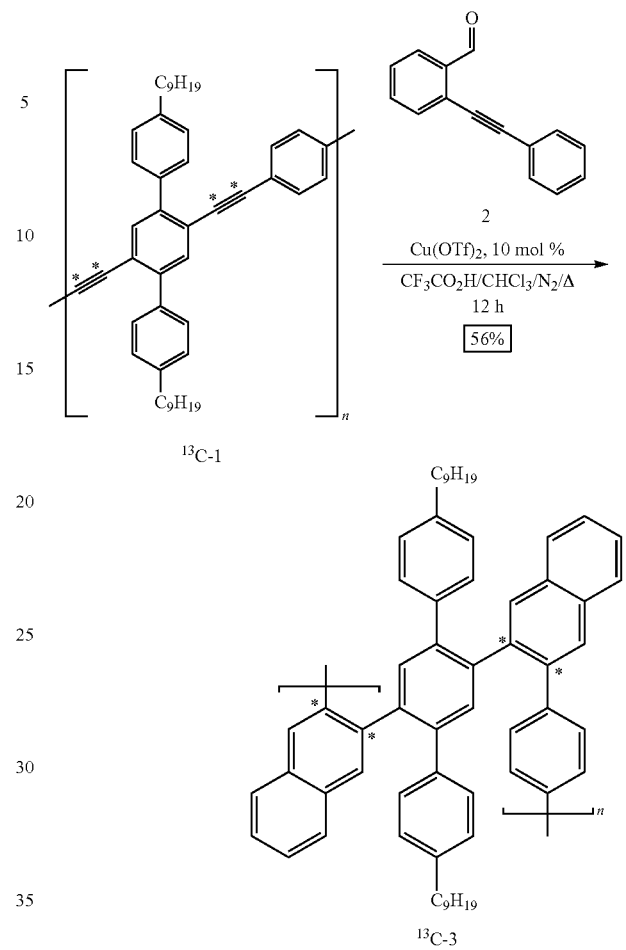

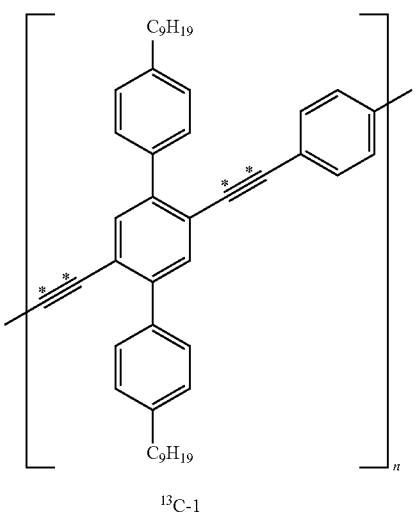

Synthesis of $^{13}$C-1: $^{13}$C-1 was synthesized under the similar conditions as PPE 1. Instead of S4, S4-$^{13}$C$_4$ (0.143 g, 0.267 mmol) and 1,4-diiodobenzene (0.089 g, 0.270 mmol) were used. $^{13}$C-1 (0.150 g, 91% yield) $^{13}$C-1: $^1$H NMR (400 MHz, CDCl$_3$) δ 7.69 (d, $J_{CH}$=3.9 Hz, 2H), 7.62 (d, $J_{HH}$=7.8 Hz, 4H), 7.29 (d, $J_{HH}$=7.8 Hz, 4H), 7.26 (s, 2H), 2.71 (t, $J_{HH}$=7.3 Hz, 4H), 1.71 (m, 4H), 1.45-1.21 (m, 24H), 0.94-0.84 (m, 6H). $^{13}$C NMR (100 MHz, CDCl$_3$) δ 131.5, 129.3, 128.3, 94.2 (d, $J_{CC}$=184.2 Hz), 91.4 (d, $J_{CC}$=184.2 Hz), 36.0, 32.1, 31.6, 29.6, 29.5, 22.8, 14.2.

Synthesis of $^{13}$C-3: $^{13}$C-3 was synthesized under the similar conditions as polymer 3. Instead of polymer 1, $^{13}$C-1 (0.020 g) was used. $^{13}$C-3 (0.015 g, 56% yield): $^1$H NMR (400 MHz, CDCl$_3$) δ 8.21-5.59 (m, 26H), 2.40 (brs, 4H), 1.70-0.36 (m, 34H). $^{13}$C NMR (100 MHz, CDCl$_3$) δ 141.5-135.6 (br), 130.8-125.2 (br), 32.1, 29.7.

TABLE 1

Molecular weight Determination of Polymers 1 and 3.

| | $M_n$ (kDa) | $M_w$ (kDa) | PDI | dn/dc (mL/g) | $D_p$ |
|---|---|---|---|---|---|
| Polymer 1 | 7.85 | 27.7 | 3.53 | 0.265 | 12 |
| Polymer 3 | 39.6 | 65.3 | 1.65 | 0.130 | 49 |
| $^{13}$C-Polymer 1 | 9.72 | 14.1 | 1.45 | 0.265 | 15 |

Atomic Force Microscopy. Sample Preparation. GNR 4 (4.6 mg) was dispersed in a solution of 1-pyrenecarboxylic acid in MeOH (0.32 mg/mL, 3.0 mL) by sonicating for 90 min. Distilled H$_2$O (10 mL) was added and the mixture was sonicated for 8 h. The dispersion was centrifuged for 1 h at 4000 rpm. The supernatant was removed and the precipitate was redispersed in distilled H$_2$O (20 mL) by sonicating for 90 min 1.0 mL of this dispersion was added to concentrated H$_2$SO$_4$ (2.0 mL). KMnO$_4$ (5.0 mg, 0.032 mmol) was added to the mixture and the solution was heated to 60° C. for 2 h. The turbidity of the solution decreased during this time. The solution was cooled to rt and 0.1 mL was added to a 0.1M NaOH solution (10 mL). The resulting solution (pH~1) was further diluted by a 20-fold excess of distilled $H_2O$. This solution was used for the AFM experiments. A drop of above solution was placed on a freshly cleaved HOPG surface (SPI grade-2). After 4 hours, the drop was absorbed onto filter paper and AFM analysis was performed on the HOPG surface.

Results. Synthesis of Graphene Nanoribbons from Conjugated Polymers. The GNR synthesis (FIG. 1) can rationally control important structural parameters (width, length, and edge functionality) and offers major advantages over existing methods. It is based on covalently modifying poly (phenylene ethynylene)s (PPEs). PPEs are a class of conductive polymers that have found use in commercial light-emitting diodes and fluorescent sensors. The synthesis is straightforward, tolerates many functional groups, and produces high molecular weight polymers. These features make PPEs ideal precursors for structurally precise GNRs.

The key transformation of the approach depicted in FIG. 1 is an annulation of each alkyne of a PPE that contains alternating terphenyl and phenyl groups (3). The annulation converts the alkynes of 3 into ortho-linked aromatic systems, transforming the PPE into a polyphenylene 4 containing alternating ortho and para linkages along its backbone. Though poly-p-phenylenes have been studied extensively as semiconducting polymers and blue-emitting materials for OLEDs, poly-o-phenylenes are very difficult to prepare and only three oligomeric examples have been reported. Oxidation of 4 under Scholl conditions provides the final GNR 5. This final oxidative carbon-carbon bond forming process is ubiquitous in the synthesis of polycyclic aromatic hydrocarbons and has been used reliably for very large systems and small GNRs. This novel annulation chemistry of PPEs provides us with unprecedented access to structurally precise GNRs.

Figure 2:
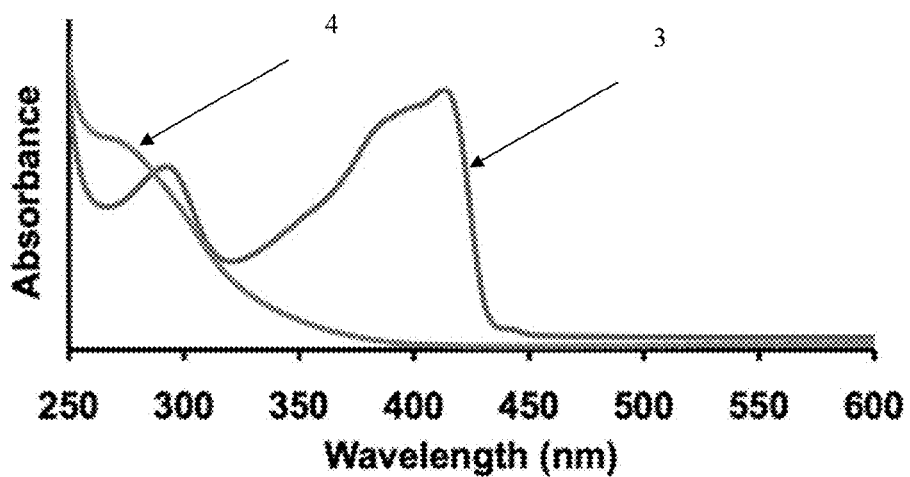
FIG. 2. Representative UV/Visible spectra of the PPE 3 and annulated polymer 4. The steric congestion of 4 reduces the effective conjugation length, shifting the absorbance of the polymer to higher energy.

Subjecting PPE 3 to Cu-catalyzed benzannulation conditions changes its properties in a manner consistent with its conversion to polyphenylene 4. Its $^1H$ and $^{13}C$ NMR and Fourier transform infrared (FT-IR) spectra are each consistent with the annulated structure. The UV/Vis spectrum of 4 (FIG. 2) is blue-shifted dramatically relative to 3 because the steric congestion around the newly installed 2,3-substituted naphthalene rings forces them to twist out of conjugation, a phenomenon that has been noted in o-linked phenylenes previously. The complete disappearance of the PPE absorbance band centered at 410 nm suggests that the annulation reaction proceeded to completion. The fluorescence spectrum of 4 also shows considerable blue shifting relative to 3, an observation that further suggests a high degree of annulation of the alkyne units.

Figure 3:
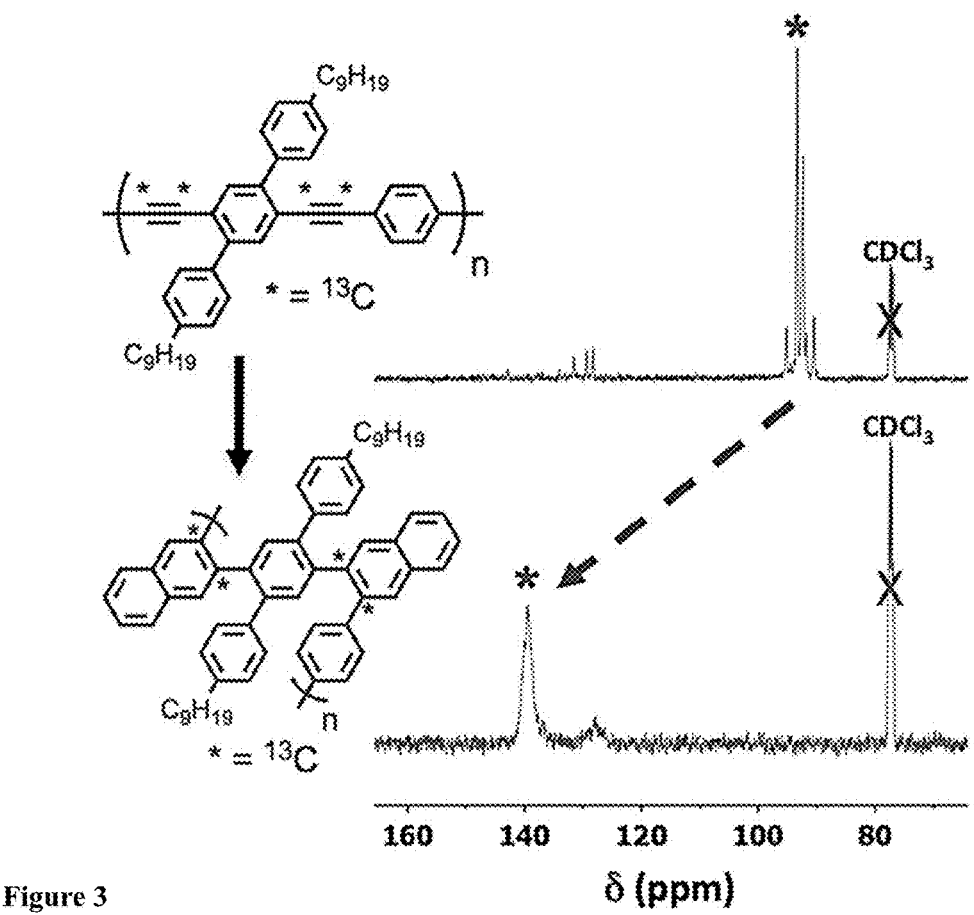
FIG. 3. Representative $^{13}C$ NMR spectra of a $^{13}C$-enriched sample of 3 that was annulated to provide $^{13}C$-enriched 4. The resonances of the enriched carbons (*) shift to the aromatic region of the spectrum, and no resonances of corresponding to residual alkynes are observed. The low-intensity resonances near 130 ppm in each spectrum correspond to the aromatic carbons of 3 and 4 that contain $^{13}C$ in natural abundance.

Further spectroscopic evidence was sought for the annulation efficiency because of the unprecedented nature of this transformation and its importance for obtaining high quality GNRs. A sample of 3 in which the alkyne carbons were isotopically enriched with $^{13}C$ (99% as compared to 1% natural abundance) was prepared. The most intense resonances of its $^{13}C$ NMR spectrum (FIG. 3, top) correspond to the $^{13}C$-labelled alkyne carbons. This sample of 3 was annulated, and the $^{13}C$ NMR spectrum of the resulting $^{13}C$-enriched 4 was obtained (red spectrum). The major resonances shift to the aromatic region of the spectrum, and no residual alkyne resonances are visible above the baseline. This experiment unambiguously demonstrates the efficiency of the annulation of the alkynes of 3, yielding the desired GNR precursors.

Figure 4:
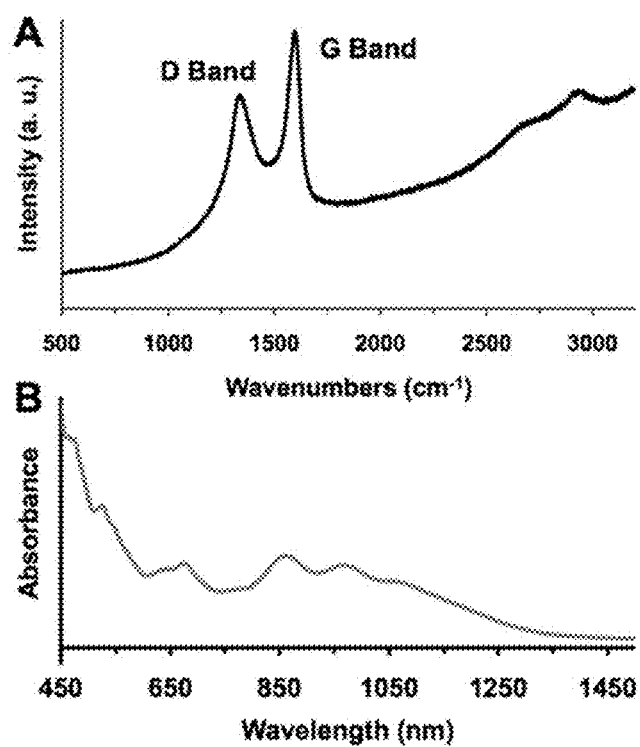
FIG. 4. A: Representative Raman spectra of GNR 5 drop-cast from $CS_2$ onto a glass slide. B: Representative UV/Vis/NIR absorbance spectrum of GNR 5.
Figure 5:
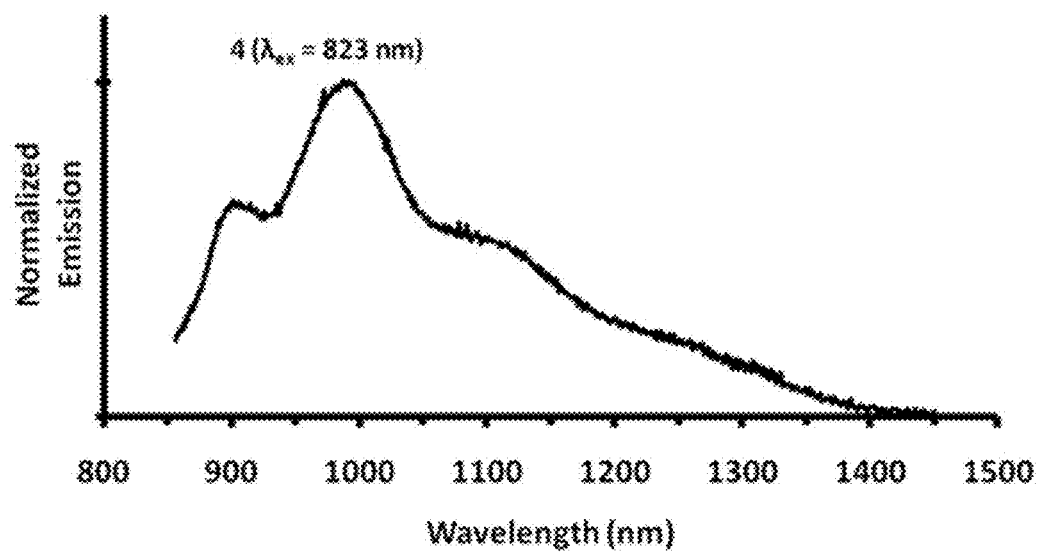
FIG. 5. Representative photoemission spectrum of graphene nanoribbon 4 (in CS$_2$).
Figure 6:
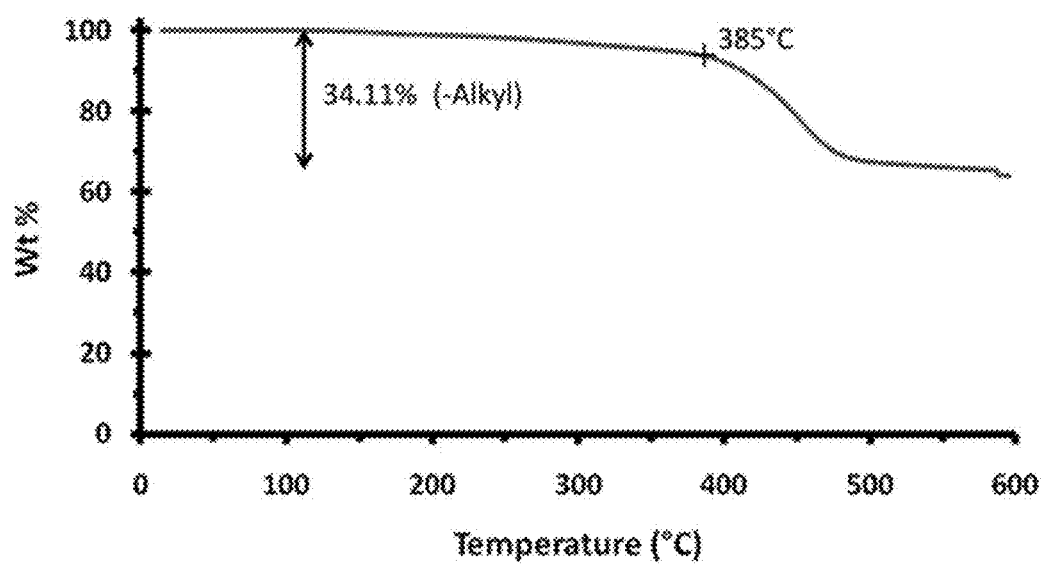
FIG. 6. Example of thermogravimetric analysis of polymer 1.
Figure 7:
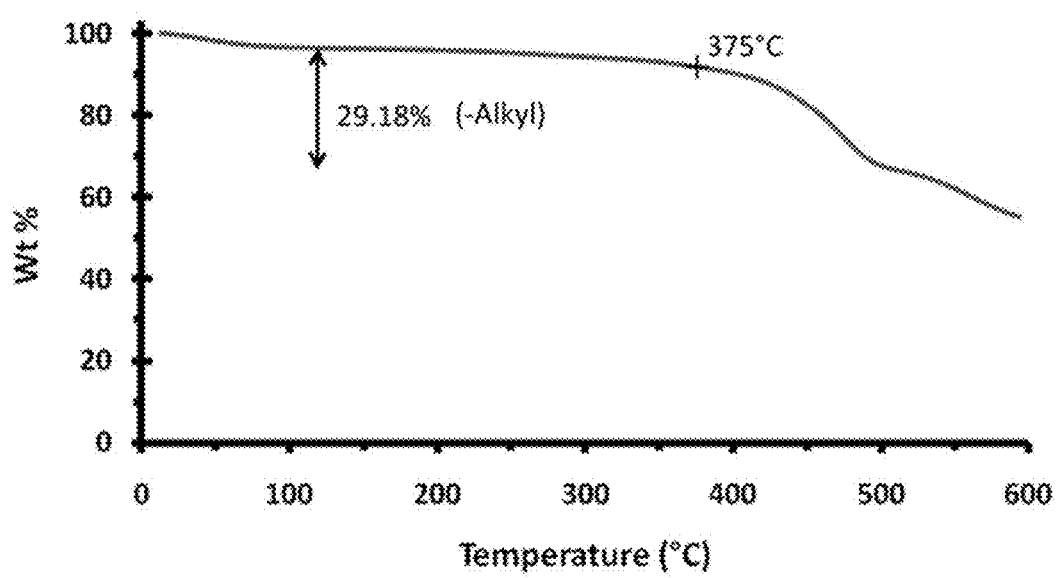
FIG. 7. Example of thermogravimetric analysis of polymer 3.
Figure 8:
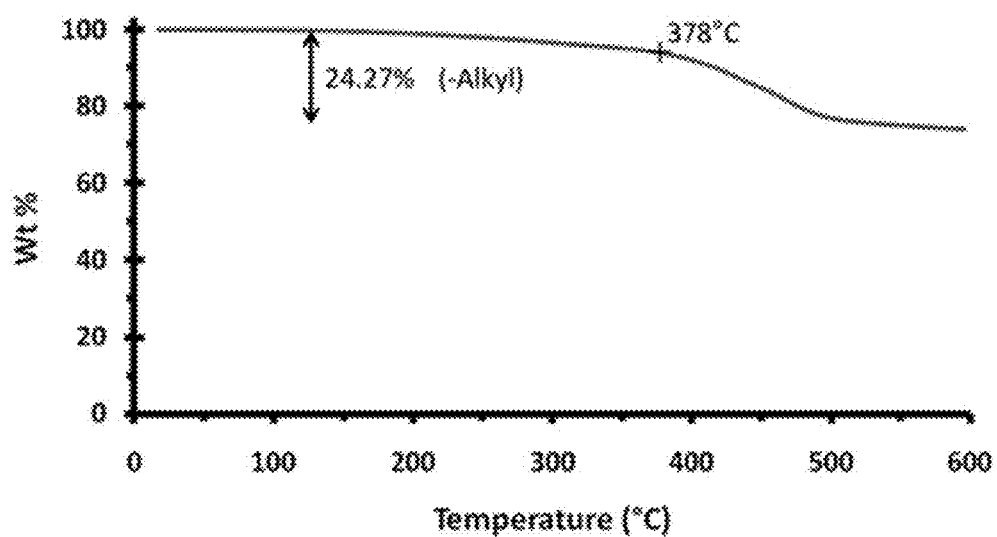
FIG. 8. Example of thermogravimetric analysis of graphene nanoribbon 4.
Figure 9:
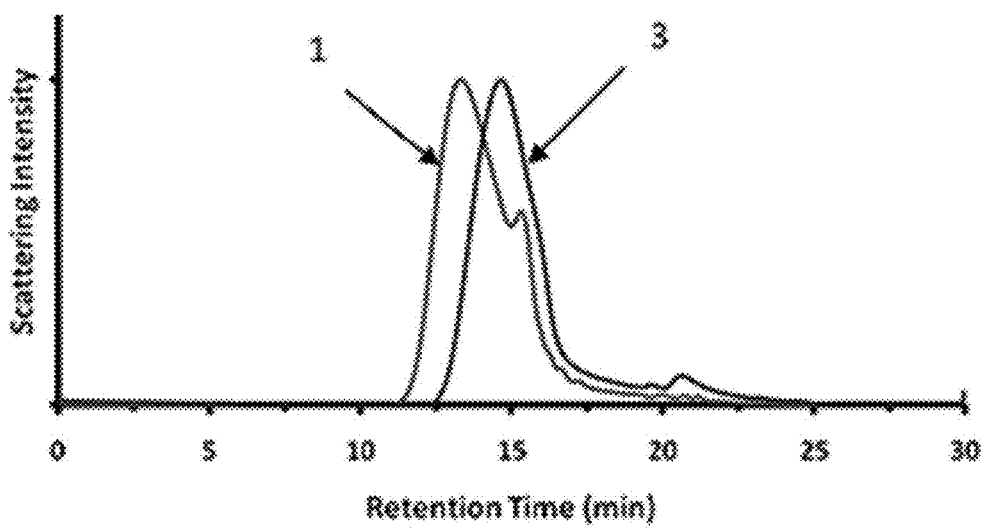
FIG. 9. Representative size-exclusion chromatograms of polymer 1 and polymer 3, as detected by their light-scattering intensity.
Figure 10:
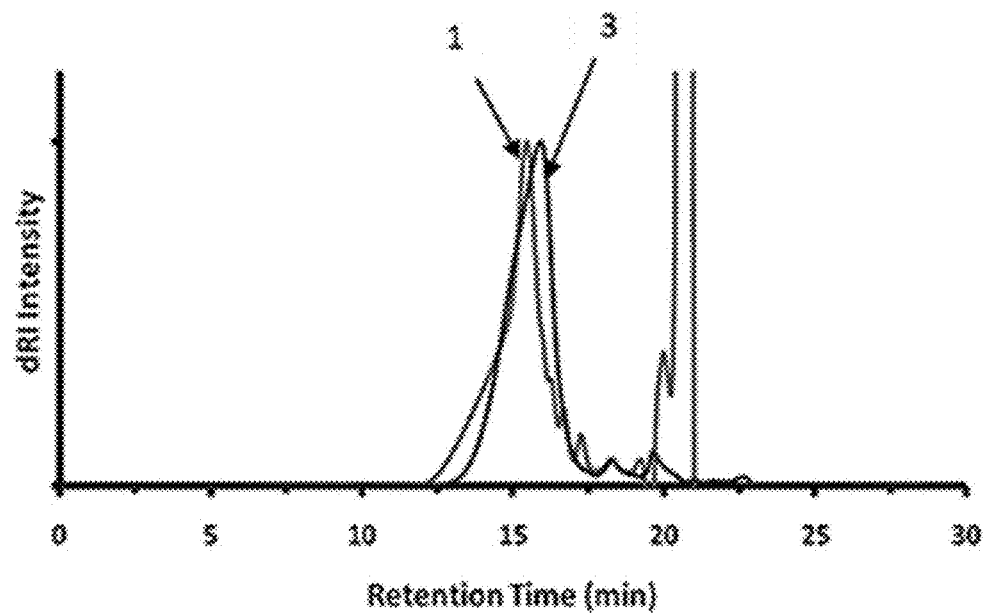
FIG. 10. Representative size-exclusion chromatograms of polymer 1 and polymer 3, as detected by changes in refractive index of the THF mobile phase.
Figure 11:
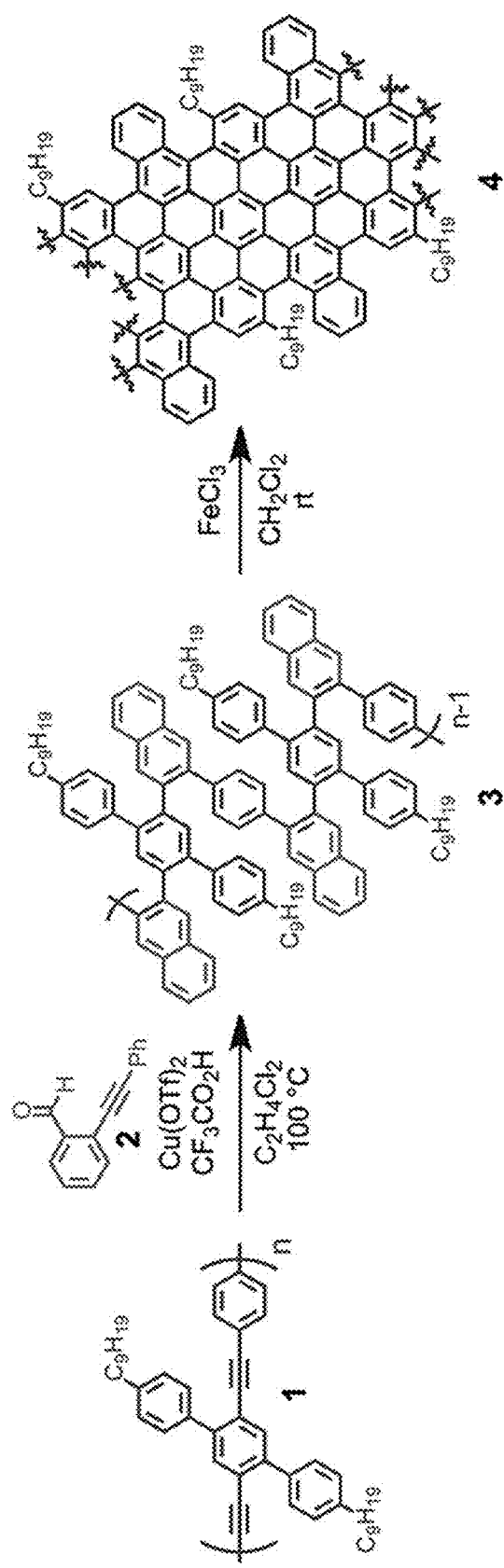
FIG. 11. Example of a two-step synthesis of a structurally precise GNR from a conjugated polymer precursor. Each alkyne of an appropriately substituted poly(phenylene ethynylene) 1 is transformed to a 2,3-disubstitued naphthalene moiety by benzaldehyde 2 under Cu(OTf)$_2$-catalyzed benzannulation conditions to provide the polyphenylene structure 3. Oxidative dehydrogenation of 3 provides the graphene nanoribbon 4.
Figure 12:
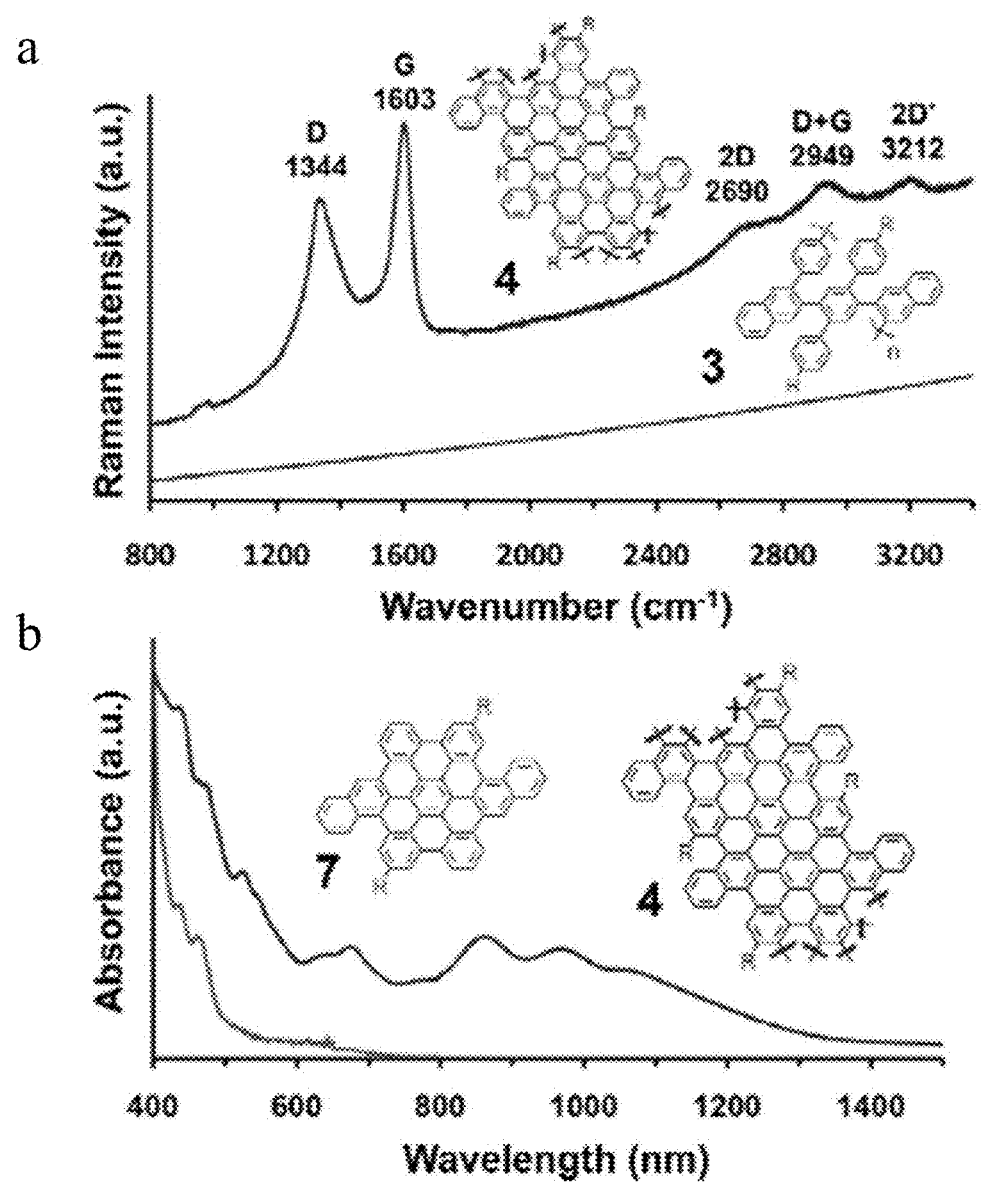
FIG. 12. Spectroscopy of GNR 4. a. Representative Raman spectra of benzannulated polymer 3 and GNR 4 obtained under the same conditions. The observed Raman bands on the GNR are labeled. b. Absorption spectra of an oxidized model compound (in 1,2-dichlorobenzene) and GNR 4 (in CS$_2$). The GNR shows a dramatic red-shift relative to its benzannulated precursor 3 indicative of its extended conjugation.

Treatment of 4 ($M_n$=25 kDa) with $FeCl_3$ in $CH_2Cl_2$ forms the GNR 5, which precipitates from the solution as a black solid. After purification, 5 was dispersed in $CS_2$, forming dark solutions that resemble black ink. The Raman spectrum of this solution drop-cast on a glass slide (FIG. 4A) shows the expected D and G bands of an aggregated GNR of this width. The higher intensity of the G relative to the D band has been noted as a sign of GNR quality in previous reports. The absorption spectrum of the $CS_2$ solution (FIG. 4B) shows a broad absorption over the visible range of the spectrum and a massive red shift of more than 900 nm relative to the 3 (compare to FIG. 2). The band edge at ~1400 nm corresponds to an optical bandgap of 0.88 eV. Dispersible GNRs of this width and length have not been reported, but the spectrum shown in FIG. 4B is quite promising because it resembles that of a dispersed carbon nanotube.

Example 2

An example of GNR preparation by a method of the present invention.

Methods Summary. Benzannulation of PPE 1: PPE 1 (0.180 g) was sonicated in $CHCl_3$ (10 mL) until finely dispersed. The solution was heated to just below boiling to dissolve the remaining polymer and sparged with $N_2$ for 20 min $Cu(OTf)_2$ (11 mg, 0.030 mmol), 2 (366 mg, 1.78 mmol), $CF_3CO_2H$ (0.14 mL, 1.8 mmol) were added. The reaction vessel was protected with a blast shield, sealed and heated to 100° C. for 11 h, and finally cooled to rt. The reaction mixture was poured into aqueous $NaHCO_3$ (saturated, 75 mL) and extracted with $CH_2Cl_2$ (3×50 mL). The combined organic layers were dried ($MgSO_4$), filtered and the solvent was evaporated. The crude product was dissolved in a minimum amount of $CH_2Cl_2$ and precipitated into a large excess of acetone (200 mL) stirring vigorously. The precipitate was collected by centrifugation and subjected to Soxhlet extraction in acetone for 24 h to afford polyphenylene 3 (147 mg, 61% yield) as a brown solid.

GNR Formation: Polymer 3 (0.050 g) was dissolved in $CH_2Cl_2$ (40 mL) under a $N_2$ atmosphere. A solution of $FeCl_3$ (0.300 g, 1.85 mmol) in $CH_3NO_2$ (2 mL) was added dropwise. The solution was stirred at room temperature for 24 h, after which it was poured into MeOH (50 mL), forming a black precipitate that was recovered by centrifugation. The black solid was redispersed in MeOH and centrifugated two additional times. Finally, the precipitate was washed in a Soxhlet extractor for 24 h using acetone as the liquid phase to provide the GNR 4 (0.044 g, 90% yield) as a black powder.

Figure 13:
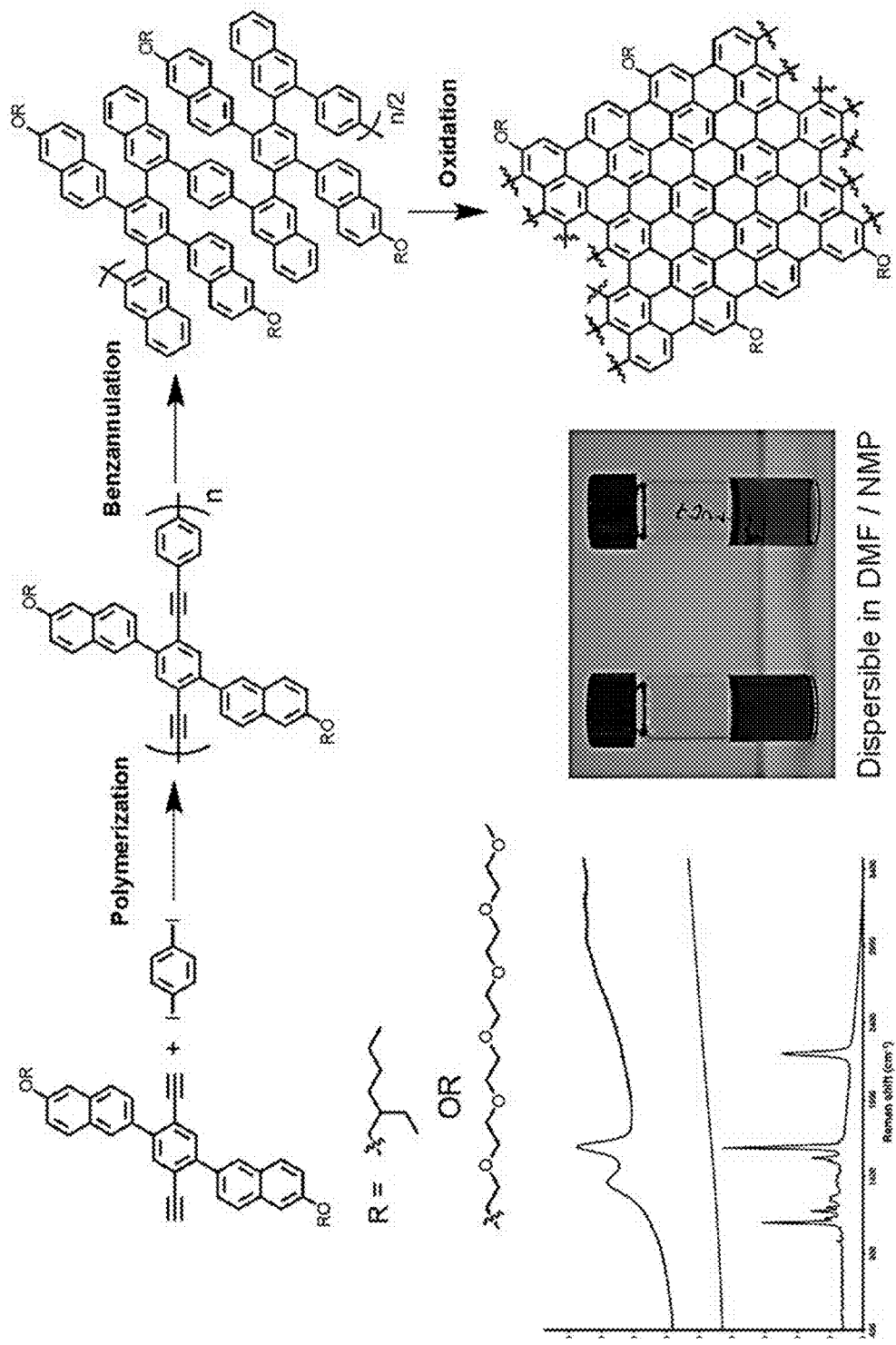
FIG. 13. Example of a graphene nanoribbon prepared from a modified poly(phenylene ethynylene) precursor with oligo(ethylene glycol) or ethylhexyloxy side chains. Photograph: dispersion of an oligo(ethylene glycol) GNR in DMF (left) and an ethylhexyl GNR in NMP (right). Inset, lower left: Representative Raman spectra of an oligo(ethylene glycol) PPE (bottom), benzannulated PPE (middle) and GNR (top).
Figure 14:
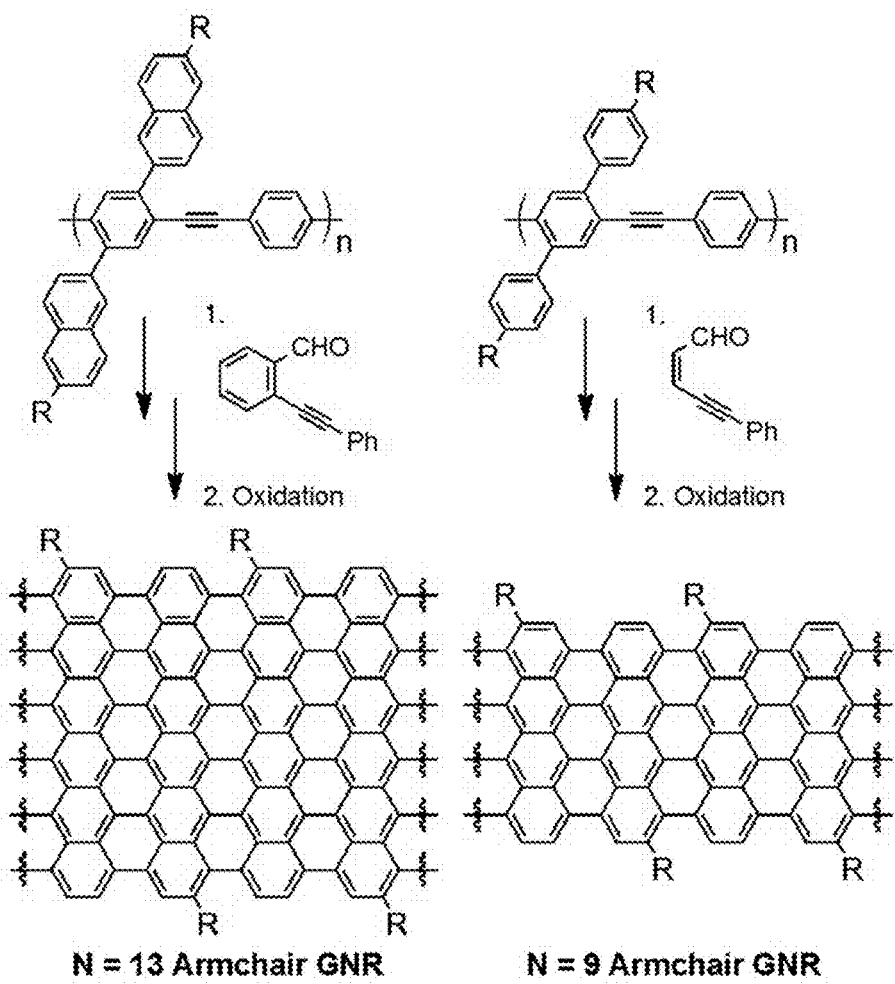
FIG. 14. Example of a synthetic strategy for graphene nanoribbons of two different widths and exact armchair edge structures.
Figure 15:
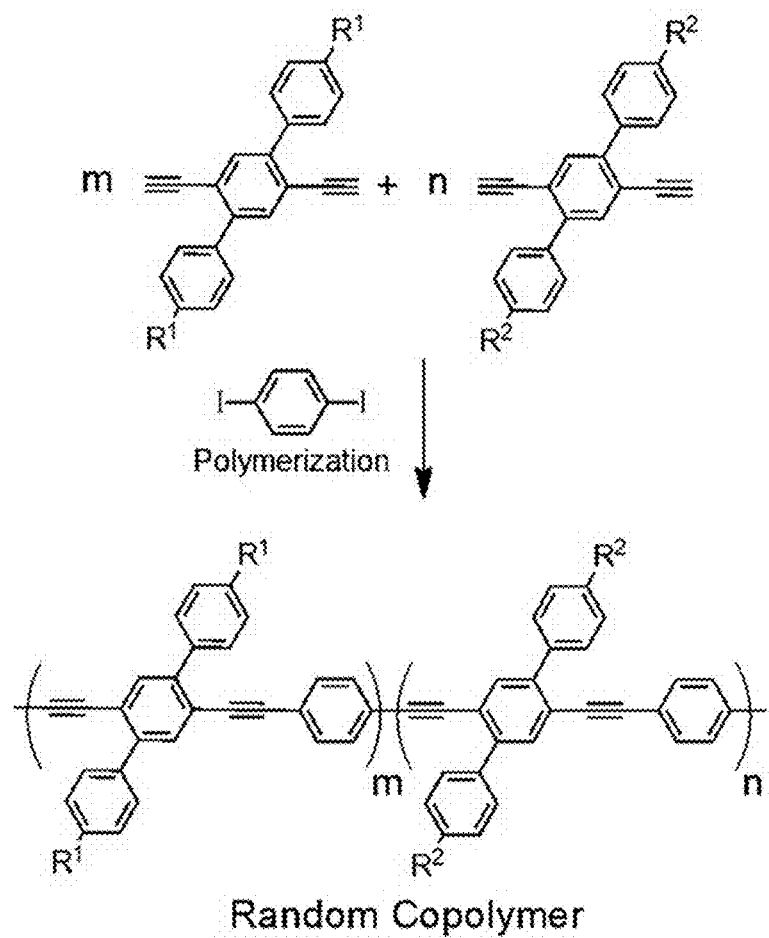
FIG. 15. Depiction of a copolymerization strategy that will allow two or more different side chains to be distributed along a PPE backbone, allowing both to be incorporated along the edge of a graphene nanoribbon.

Results and Discussion. The p-terphenyl-alt-phenyl PPE 1 was obtained by copolymerizing the appropriate terphenyl dialkyne monomer and 1,4-diiodobenzene under Sonogashira cross-coupling conditions. A substoichiometric amount of a monofunctional aryl iodide, 4-iodoanisole, was used to control the polymer's molecular weight and end-group identity. Nevertheless, 1 is insoluble in the reaction mixture at molecular weights approaching 100 kDa and partially precipitates during the polymerization. As a result, a bimodal molecular weight distribution ($M_n$=7.85 kDa; $M_w$=27.7 kDa; PDI=3.53) was obtained by size exclusion chromatography, consisting of a low molecular weight main peak with a high molecular weight shoulder (FIG. 13). These molecular weights were determined by multi-angle light scattering, a direct measure of the polymer mass that does not rely on comparisons to polymer standards of questionable applicability. Despite its broad molecular weight distribution, 1 was not separated into high and low molecular weight fractions because it was found that the shorter chains were easily removed after the benzannulation step (see below). It was estimated the $D_p$ of the high molecular weight fraction of 1 to be approximately five times higher than those found in other bottom-up GNR syntheses, making it an appropriate system in which to evaluate the synthetic approach.

PPE 1 was benzannulated [3 equiv. 2 per alkyne, 3 equiv. $CF_3CO_2H$, 0.05 equiv. $Cu(OTf)_2$], after which polyphenylene 3 was isolated by precipitation from $CH_2Cl_2$ into acetone, followed by Soxhlet extraction using acetone as the liquid phase. Size exclusion chromatography analysis of the acetone-insoluble material showed a monomodal distribution of chain sizes whose molecular weight and polydispersity ($M_n$=39.6 kDa, PDI=1.65, $D_p$=49) correspond to the benzannulation of the higher molecular weight portion of 1. This material was taken forward in the GNR synthesis. Steric hindrance along the polymer backbone prevents 3 from adopting a planar conformation and it is far more soluble in organic solvents than 1. Despite its higher molecular weight, polyphenylene 3 is retained longer by the SEC columns relative to its PPE precursor 1, which is attribute to the polymer adopting a more compact solvated structure as a consequence of its steric demands. As a result, the polymer chains of 3 adopt smaller hydrodynamic volumes than random-coil polymer chains of comparable molecular weight.

The efficiency of the benzannulation of PPE 1 was characterized using a full complement of spectroscopic measurements. The inability of adjacent aromatic rings in 3 to adopt coplanar conformations induces a significant blue shift in its UV/Vis absorption spectrum relative to its PPE precursor 1. The $\lambda_{max}$ of 3 is shifted 140 nm lower than that of 1. If the benzannulation were inefficient, residual alkyne-containing subunits would cause 3 to absorb in this region or at longer wavelengths, yet 3 does not absorb within this spectral range. The photoemission of 3 also occurs at significantly shorter wavelength ($\lambda_{max}$=400 nm, than 1 ($\lambda_{max}$=520 nm), which also indicates the reduced conjugation length of 3 and thus, efficient benzannulation. Fourier transform infrared (FTIR) spectroscopy of 3 showed increased $sp^2$ C—H stretches at 3030 cm$^{-1}$ from the newly installed naphthalene rings, as well as significant changes in the 500-1500 cm$^{-1}$ region that suggest major modifications to the structure of 3 relative to its PPE precursor 1.

An isotopic labeling study provided direct evidence for the high efficiency of the benzannulation. A sample of PPE 1 with $^{13}$C-enriched alkyne carbons was prepared by employing trimethylsilylacetylene-$^{13}C_2$ in the synthesis of its dialkyne monomer. The most intense resonances of its $^{13}$C NMR spectrum are centered at 92.8 ppm and correspond to the two $^{13}$C-enriched alkyne carbons. The three small resonances at 128.3, 129.3 and 131.5 ppm correspond to aromatic carbons with naturally abundant amounts of $^{13}$C and have identical chemical shifts as the three most intense aromatic resonances in the spectrum of unlabeled 1. After benzannulation, the $^{13}$C-enriched alkyne signals were shifted cleanly to a broad peak centered at 139.5 ppm and no residual alkyne resonances are visible above the baseline (FIG. 19d). Much like model compound 6, both the $^{13}$C-labeled and unlabeled $^1$H and $^{13}$C NMR spectra of the benzannulated polymer show significant peak broadening as a consequence of hindered rotation about the newly installed 2,3-disubstituted naphthalene moieties.

This isotopic labeling experiment, in concert with the spectroscopic and SEC characterization of the polymer 3, unambiguously demonstrates that this unprecedented transformation of PPE 1, the key step of the synthetic approach, proceeds efficiently.

Polyphenylene 3 was oxidized to the GNR 4 using $FeCl_3$ in a mixture of $CH_3NO_2$ and $CH_2Cl_2$. The GNR 4 precipitated from the solution as a black solid, which was again purified by Soxhlet extraction using acetone as the liquid phase. n-nonyl groups are insufficient to solubilize 4 in most organic solvents, but it was possible to disperse the ribbons in $CS_2$ or 1,2-dichlorobenzene (DCB), enabling their spectroscopic characterization. The Raman spectrum (488 nm excitation) of a $CS_2$ solution of 4 drop-cast on a Si wafer (FIG. 20a) is indicative of a graphitic material and shows the D and G bands of an aggregated GNR at 1344 cm$^{-1}$ and 1603 cm$^{-1}$, respectively. The higher intensity of the G relative to the D band has been noted as a sign of GNR quality in previous reports. The spectrum also includes the 2D feature at 2690 cm$^{-1}$, the disorder-induced combination mode (D+G) at 2949 cm$^{-1}$, and the 2D' band at 3212 cm$^{-1}$. Drop-cast films of the precursor polymer 3 exhibit none of these spectral features.

$CS_2$ solutions of 4 (FIG. 20b) absorb light over the entire UV and visible ranges of the spectrum, a red shift of more than 900 nm relative to its precursor 3 (compare to FIG. 19b).

This red shift is far larger than those observed in the synthesis of shorter GNRs, indicating efficient dehydrogenation that gives rise to extended conjugation along the length of the GNR 4. FTIR spectroscopy indicates that the ribbons retain their n-nonyl solubilizing groups, as evidenced from the $sp^3$-hybridized C—H stretches centered at 2919 cm$^{-1}$. The FTIR spectrum shows highly attenuated $sp^2$-hybridized C—H stretches that were present at 3030 cm$^{-1}$ in the spectra of both 1 and 3, also confirming that the oxidation proceeded to completion. Finally, the C—C stretching region of the spectrum simplified dramatically due to the high symmetry of the nanoribbon product. GNR 4 also showed excellent thermal stability expected for a graphitic material. Thermogravimetric analysis of 4 indicated a 24.3% loss of mass near 378° C., corresponding to loss of the alkyl chains, followed by no additional loss of mass to at least 600° C.

Aggregated ribbons are observed by transmission electron microscopy of dilute dispersions of 4 nebulized onto holey carbon grids. Atomic force micrographs of 4 oxidized by $KMnO_4/H_2SO_4$ showed smaller aggregates with high aspect ratios. The benzannulation of PPEs described here provides a bottom-up synthesis of GNRs, allowing control of width, edge structure, and peripheral functionality.

While the invention has been particularly shown and described with reference to specific embodiments (some of which are preferred embodiments), it should be understood by those having skill in the art that various changes in form and detail may be made therein without departing from the spirit and scope of the present invention as disclosed herein.

What is claimed is:

1. A method for making a graphene nanoribbon comprising the steps of:

a) contacting a poly(phenylene ethynylene) (PPE) polymer, an annulating compound, and a catalyst system comprising a metal catalyst and a protic acid, such that the PPE polymer is arylannulated;

b) oxidizing the arylannulated polymer product from a), such that a graphene nanoribbon is formed.

2. The method of claim 1, wherein the PPE polymer has the following structure:

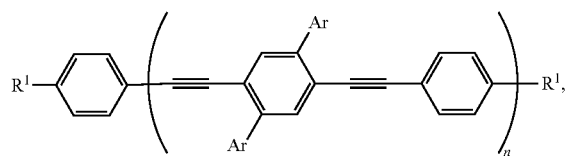

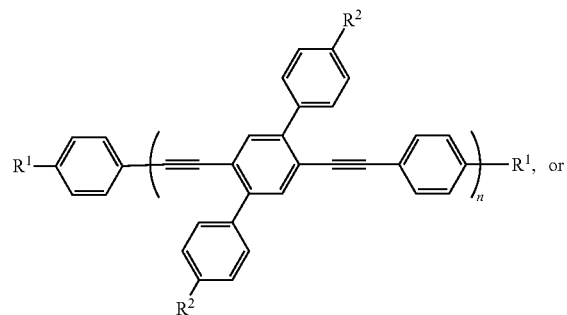

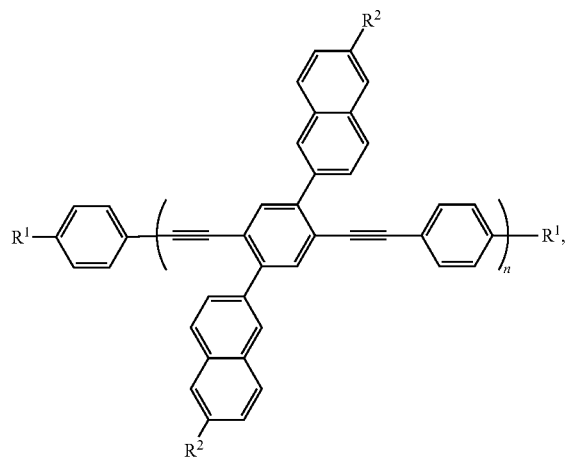

wherein Ar is an aryl group having from 6 carbons to 24 carbons,

R$^1$ and R$^2$ are, at each occurrence in the PPE polymer, independently selected from the group consisting of H, alkyl, aryl, ether, thioether, ester, carboxylic acid, amide, halide, and azide groups, and n is from 10 to 500.

3. The method of claim 1, wherein the annulating compound comprises an aryl ethynylene group, and an en-al group or an aryl aldehyde group.

4. The method of claim 1, wherein the metal catalyst is a copper(II) salt or a zinc(II) salt.

5. The method of claim 4, wherein the copper(II) salt is selected from the group consisting of Cu(OTf)$_2$, Cu(acetate)$_2$, Cu(trifluoroacetate)$_2$, Cu(halide)$_2$, Cu(sulfate)$_2$, and Cu(II) oxide.

6. The method of claim 4, wherein the zinc (II) salt is selected from the group consisting of Zn(OTf)$_2$, Zn(acetate)$_2$, Zn(trifluoroacetate)$_2$, Zn(halide)$_2$, Zn(sulfate)$_2$, and Zn oxide.

7. The method of claim 1, wherein the oxidizing step is carried out in solution and the concentration of arylannulated polymer is present at a concentration of 50 mM or less.

8. The method of claim 1, wherein the PPE polymer has the following structure:

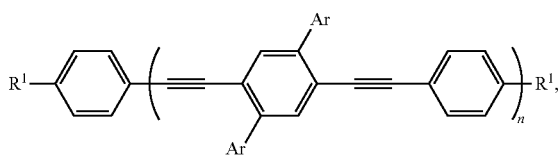

wherein Ar is an aryl group having from 6 carbons to 24 carbons,

R$^1$ and R$^2$ is independently selected from the group consisting of H, alkyl, aryl, ether, thioether, ester, carboxylic acid, amide, halide, and azide groups, and n is from 10 to 500.

9. The method of claim 1, wherein the PPE polymer has the following structure:

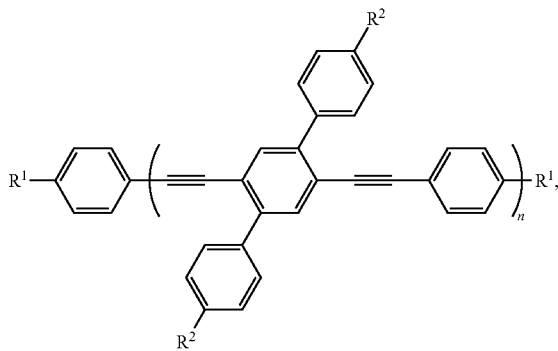

wherein R$^1$ and R$^2$ are, at each occurrence in the PPE polymer, independently selected from the group consisting of H, alkyl, aryl, ether, thioether, ester, carboxylic acid, amide, halide, and azide groups, and n is from 10 to 500.

10. The method of claim 1, wherein the PPE polymer has the following structure:

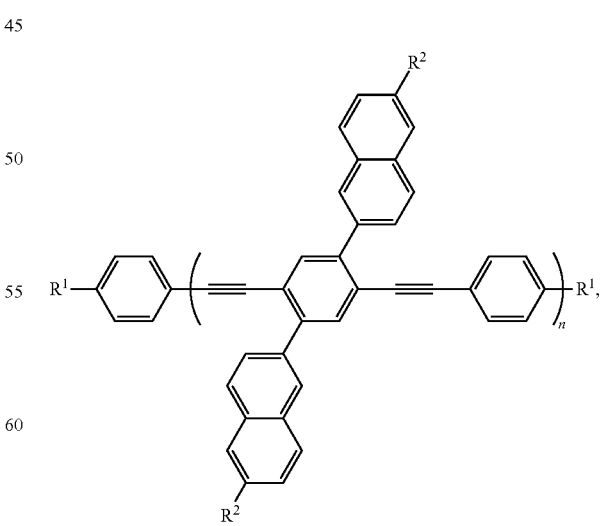

wherein R$^1$ and R$^2$ are, at each occurrence in the PPE polymer, independently selected from the group consisting of H, alkyl, aryl, ether, thioether, ester, carboxylic acid, amide, halide, and azide groups, and n is from 10 to 500.

11. The method of claim 1, wherein the metal catalyst is a copper(II) salt.

12. The method of claim 1, wherein the metal catalyst is a zinc(II) salt.

13. A graphene nanoribbon (GNR) having the following structure:

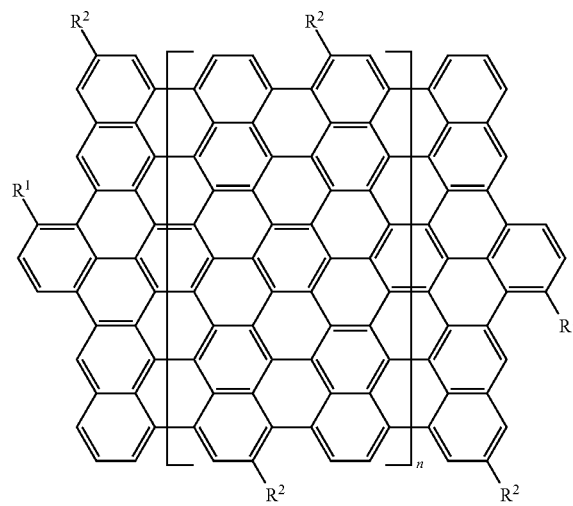

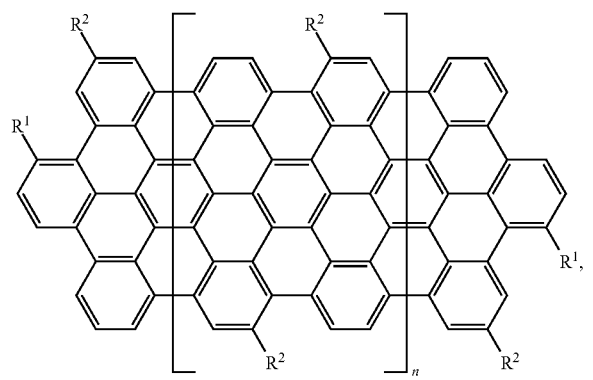

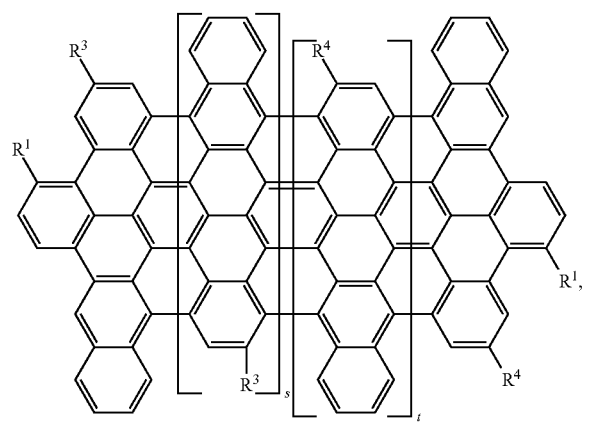

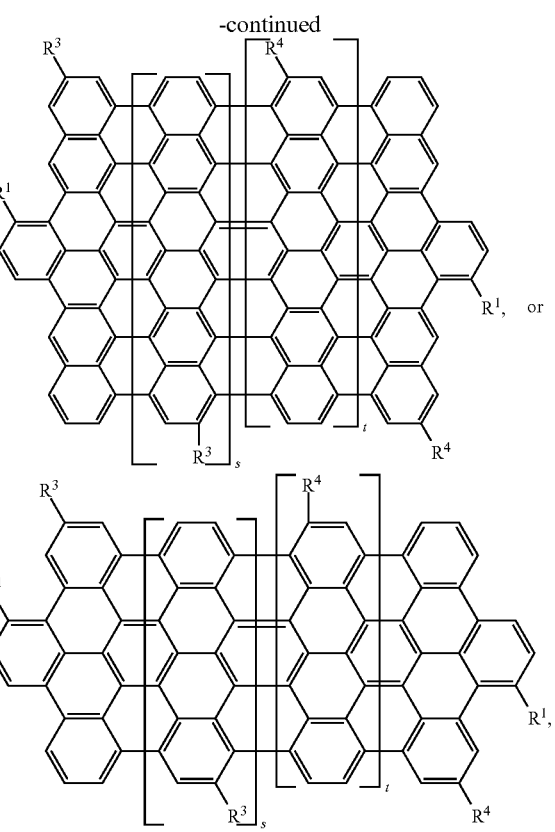

$R^1$, $R^2$, $R^3$, and $R^4$ are, at each occurrence in the GNR, independently selected from the group consisting of H, alkyl, aryl, ether, thioether, ester, carboxylic acid, amide, halide, and azide groups, n is from 10 to 500, and s+t is from 10 to 500, wherein $R^1$, $R^2$, $R^3$, and $R^4$ are not each H.

14. The GNR of claim 13, wherein the GNR has a length of 10 to 500 nm.

15. The GNR of claim 13, wherein the GNR has a width of 1.0 to 1.2 nm, wherein the width does not include $R^1$, $R^2$, $R^3$, and $R^4$.

16. A device comprising a graphene nanoribbon of claim 13.

17. The device of claim 16, where the device is selected from a transistor, a solar cell, and a light emitting diode.

18. The graphene nanoribbon (GNR) of claim 13, wherein the GNR has the following structure:

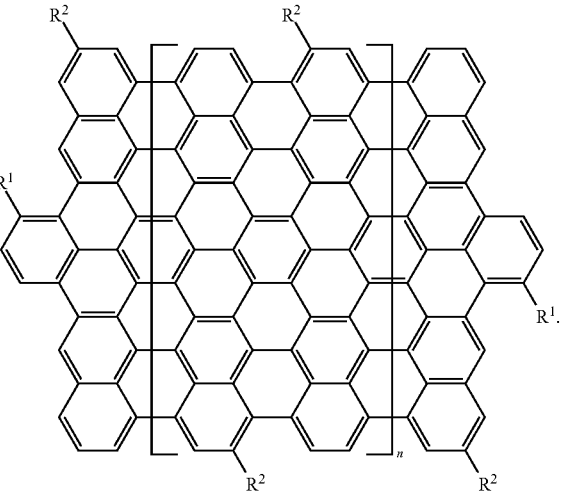

19. The graphene nanoribbon (GNR) of claim 13, wherein the GNR has the following structure:
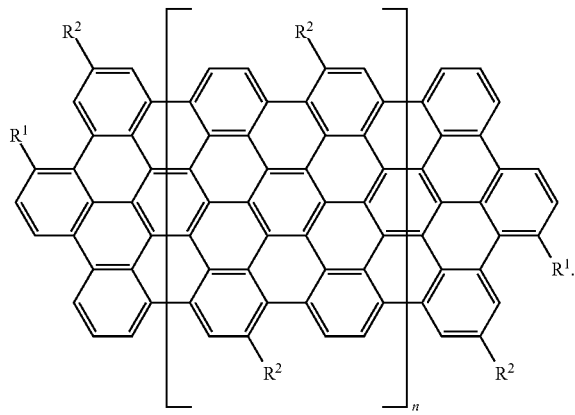
20. The graphene nanoribbon (GNR) of claim 13, wherein the GNR has the following structure:
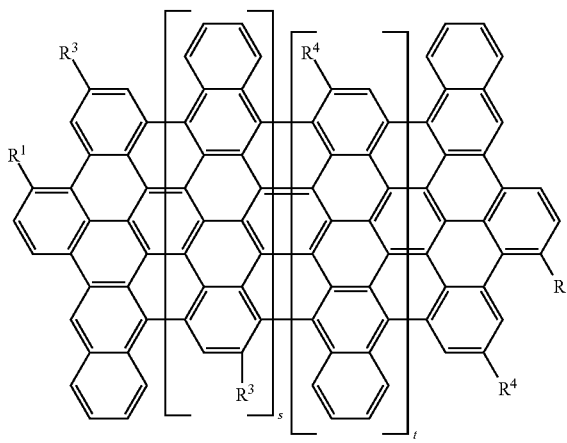
21. The graphene nanoribbon (GNR) of claim 13, wherein the GNR has the following structure:
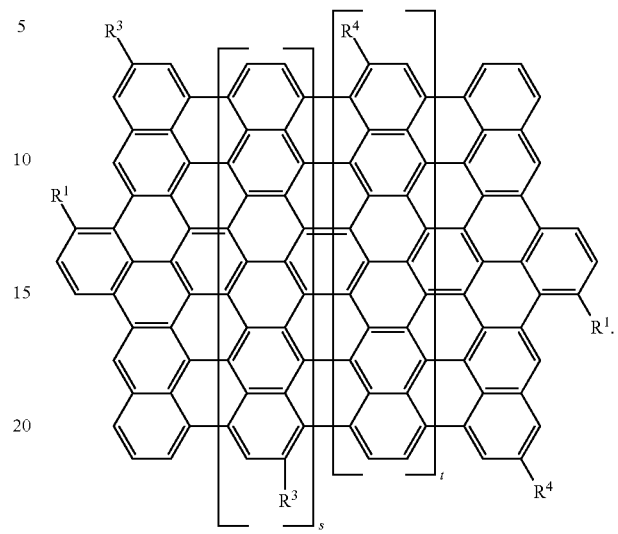
22. The graphene nanoribbon (GNR) of claim 13, wherein the GNR has the following structure:
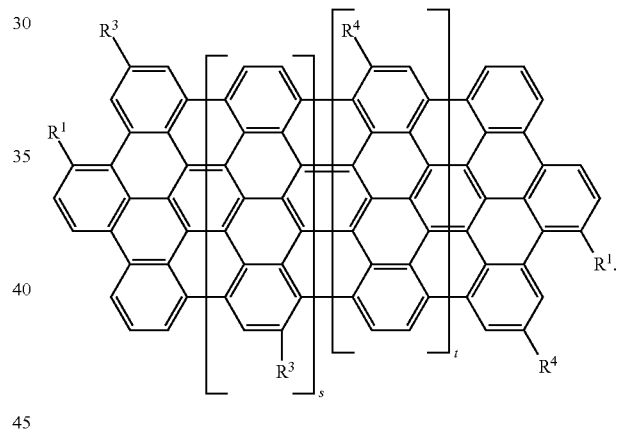
* * * * *